US009701720B2

(12) United States Patent
Schief et al.

(10) Patent No.: US 9,701,720 B2
(45) Date of Patent: Jul. 11, 2017

(54) EPITOPE-SCAFFOLD IMMUNOGENS AGAINST RESPIRATORY SYNCYTIAL VIRUS (RSV)

(71) Applicant: University of Washington through its Center for Commercialization, Seattle, WA (US)

(72) Inventors: William R. Schief, Encinitas, CA (US); Bruno E. Correia, San Diego, CA (US)

(73) Assignee: University of Washington Through Its Center For Commercialization, Seattle, WA (US)

( * ) Notice: Subject to any disclaimer, the term of this patent is extended or adjusted under 35 U.S.C. 154(b) by 165 days.

(21) Appl. No.: 14/387,476

(22) PCT Filed: Apr. 5, 2013

(86) PCT No.: PCT/US2013/035408
§ 371 (c)(1),
(2) Date: Sep. 23, 2014

(87) PCT Pub. No.: WO2013/152274
PCT Pub. Date: Oct. 10, 2013

(65) Prior Publication Data
US 2015/0050306 A1 Feb. 19, 2015

Related U.S. Application Data

(60) Provisional application No. 61/620,797, filed on Apr. 5, 2012, provisional application No. 61/620,804, filed on Apr. 5, 2012.

(51) Int. Cl.

| | |
|---|---|
| *A61K 38/00* | (2006.01) |
| *C07K 14/005* | (2006.01) |
| *A61K 39/12* | (2006.01) |
| *C12N 7/00* | (2006.01) |
| *A61K 39/155* | (2006.01) |
| *G01N 33/569* | (2006.01) |
| *A61K 39/00* | (2006.01) |

(52) U.S. Cl.
CPC ............ *C07K 14/005* (2013.01); *A61K 39/12* (2013.01); *A61K 39/155* (2013.01); *C12N 7/00* (2013.01); *G01N 33/56983* (2013.01); *A61K 2039/5258* (2013.01); *A61K 2039/55555* (2013.01); *A61K 2039/6075* (2013.01); *C12N 2760/18522* (2013.01); *C12N 2760/18523* (2013.01); *C12N 2760/18534* (2013.01); *C12N 2760/18571* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 5,334,394 | A | 8/1994 | Kossovsky et al. |
| 5,770,380 | A | 6/1998 | Hamilton et al. |
| 7,097,841 | B2 | 8/2006 | Carter et al. |
| 7,229,618 | B2 | 6/2007 | Johnson et al. |
| 7,229,624 | B2 | 6/2007 | Renner et al. |
| 7,700,720 | B2 | 4/2010 | Tous et al. |
| 2011/0236408 | A1 | 9/2011 | Morrison et al. |
| 2012/0315270 | A1 | 12/2012 | McLellan et al. |
| 2015/0050306 | A1 | 2/2015 | Schief et al. |

FOREIGN PATENT DOCUMENTS

| | | | |
|---|---|---|---|
| AU | 2011311946 | | 10/2014 |
| CN | 1668335 | A | 9/2005 |
| CN | 103282378 | A | 9/2013 |
| CN | 201180058569.8 | | 3/2015 |
| EP | 2834263 | | 2/2015 |
| EP | 2625194 | | 8/2015 |
| JP | 2014-502143 | | 1/2014 |
| WO | 2008/025015 | | 2/2008 |
| WO | 2009/079796 | | 7/2009 |
| WO | 2009/100376 | | 8/2009 |
| WO | 2011/050168 | | 4/2011 |
| WO | 2012/048115 | | 4/2012 |
| WO | 2013/152274 | | 10/2013 |

OTHER PUBLICATIONS

McClellan et al. J Mol Biol. 2011 vol. 409(5):853-66.*
Correia et al. JMB 2011 vol. 405, pp. 284-297.*
McClellan et al., 2013 Science vol. 340, p. 1114.*
Zhu et al. (2011) "Analysis of respiratory syncytial virus preclinical and clinical variants resistant to neutralization by monoclonal antibodies palivizumab and/or motabvizumab," Journal Infect Dis, 203(5):674-82.
Wilson et al. (1992) "Hepatocyte-directed gene transfer in vivo leads to transient improvement of hypercholesterolemia in low density lipoprotein receptor-deficient rabbits," J. Biol. Chem. 267:963-967.
Wu, et al., (2010), "Rational Design of Envelope Identifies Broadly Neutralizing Human Monoclonal Antibodies to HIV-1," Science 329:856.
Rohl et al., (2004), "Protein structure prediction using Rosetta," Methods in Enzymology 383: 66-93.
McLellan et al., "Design and Characterization of Epitope Scaffold Immunogens that present the Motavizumab Epitope from Respiratory Syncytial Virus," J. Mol. Biol. (2011) 409, 853-866.
Wu, et al., (2007) "Development of Motavizumab an ultra-potent antibody for the prevention of respiratory Syncytial virus infection in the upper and lower respiratory tract," Journal of Molecular Biology, 368(3): 652-665.
Zlotnick et al., (1996) "Dimorphism of hepatitis B virus capsids is strongly influences by the C-terminus of the capsid protein," Biochemistry, 35(23): 7412-21.

(Continued)

*Primary Examiner* — Shanon A Foley
*Assistant Examiner* — Myron Hill
(74) *Attorney, Agent, or Firm* — McDonnell Boehnen Hulbert & Berghoff LLP

(57) ABSTRACT

The present invention provides polypeptides and compositions thereof for treating or limiting respiratory syncytial virus infection, and computational methods for designing such polypeptides.

7 Claims, 8 Drawing Sheets

(56) References Cited

OTHER PUBLICATIONS

Wynne et al., (1999), "The crystal structure of the human hepatitis B virus capsid," Mol Cell, 3(6):771-80.
Bradley, et al., (2006), "Improved beta-proteins structure prediction by multilevel optimization of nonlocal strand pairing and local backbone conformation," Proteins, 65(4): 922-9.
Simons, et al., (1997), "Assembly of protein tertiary structures from fragments with similar local sequences using simulated annealing and Bayesian scoring functions," J Mol Biol., 268(1); 209-25.
International Search Report for PCT/US2011/05511, mailed Apr. 27, 2012.
International Search Report for PCT/US2013/035488, mailed Aug. 19, 2013.
McLellan et al., (2011) "Structure of Respiratory Syncytial virus fusion glycoprotein in the postfusion conformation reveals preservation of neutralizing epitopes," Journal of Virology, 85(15): 7788-7796.
McLellan et al., (2010) "structure of a major antigenic site on the respiratory syncytial virus fusion glycoprotein in complex with neutralizing antibody 101F," Journal of Virology, 84(23): 12236-12244.
Adams et al. (Nov. 2002) "PHENIX: building new software for automated crystallographic structure determination," Acta Crystallographica Section D: Biological Crystallography, 58(Pt 11):1948-1954.
Alexander et al. (Dec. 1994) "Development of high potency universal DR-restricted helper epitopes by modification of high affinity DR-blocking peptides," Immunity, 1(9):751-761.
Arbiza et al. (Sep. 1992) "Characterization of two antigenic sites recognized by neutralizing monoclonal antibodies directed against the fusion glycoprotein of human respiratory syncytial virus," Journal of General Virology, 73(Pt 9)2225-2234.
Aricescu et al. (Oct. 2006) "A time- and cost-efficient system for high-level protein production in mammalian cells," Acta Crystallographica Section D: Biological Crystallography, 62(Pt 10):1243-1250.
Barourch et al. (Jul. 2005) "A human T-cell leukemia virus type 1 regulatory element enhances the immunogenicity of human immunodeficiency virus type 1 DNA vaccines in mice and nonhuman primates," Journal of Virology, 79 (14):8828-8834.
Beeler and K. van Wyke Coelingh (Jul. 1989) "Neutralization epitopes of the F glycoprotein of respiratory syncytial virus: effect of mutation upon fusion function," Journal of Virology, 63(7):2941-2950.
Bryson et al. (Jul. 2005) "Protein structure prediction servers at University College London," Nucleic Acids Research, 33(Web Server issue):W36-W38.
Burton (Oct. 2010) "Scaffolding to build a rational vaccine design strategy," Proceedings of the National Academy of Sciences USA, 107(42):17859-17860.
Chargelegue et al. (Mar. 1998) "A Peptide Mimic of a Protective Epitope of Respiratory Syncytial Virus Selected from a Combinatorial Library Induces Virus-Neutralizing Antibodies and Reduces Viral Load In Vivo," Journal of Virology, 72 (3):2040-2046.
CN 1st Office Action dated Apr. 30, 2014.
Correia et al. (Jan. 2011) "Computational protein design using flexible backbone remodeling and resurfacing: case studies in structure-based antigen design," Journal of Molecular Biology, 405(1):284-297.
Correia et al. (Sep. 2010) "Computational Design of Epitope-Scaffolds Allows Induction of Antibodies Specific for a Poorly Immunogenic HIV Vaccine Epitope," Structure, 18(9)1116-1126.
Correia et al. (Mar. 2014) "Proof of principle for epitope-focused vaccine design," Nature, 507(7491):201-206.
Das and D. Baker (Jul. 2008) "Macromolecular Modeling with Rosetta," Annual Review of Biochemistry, 77:363-382.
Emsley and K. Cowtan (Dec. 2004) "Coot: model-building tools for molecular graphics," Acta Crystallographica Section D: Biological Crystallography, 60(Pt 12 Pt 1):2126-2132.
EP Intention to Grant dated Mar. 4, 2015 for EP 2625194.

EP Office Action dated Mar. 28, 2014 for EP 2625194.
EP Office Action dated Nov. 17, 2014 for EP 2625194.
First Examination Report dated Aug. 6, 2014 for AU 2011311946.
GenBank: AAS93649.1. Fusion protein [Human respiratory syncytial virus]. (May 2005) available online at: http://www.ncbi.nlm.nih.gov/protein/AAS93649.
Groothuis et al. (Apr. 1995) "Respiratory syncytial virus (RSV) infection in preterm infants and the protective effects of RSV immune globulin (RSVIG). Respiratory Syncytial Virus Immune Globulin Study Group," Pediatrics, 95(4):463-467.
Hallak et al. (Jun. 2000) "Iduronic acid-containing glycosaminoglycans on target cells are required for efficient respiratory syncytial virus infection," Virology, 271(2):264-275.
International Search Report and Written Opinion dated Sep. 21, 2011 for PCT/US2010/053558 filed Oct. 21, 2010, 22 pages.
International Search Report and Written Opinion dated Apr. 27, 2012 for PCT/US2011/055113 filed Oct. 6, 2011.
International Search Report and Written Opinion dated Aug. 19, 2013 for PCT/US2013/035408 filed Apr. 5, 2013.
Johnson et al. (Nov. 1997) "Development of a humanized monoclonal antibody (MEDI-493) with potent in vitro and in vivo activity against respiratory syncytial virus," Journal of Infectious Diseases, 176(5):1215-1224.
JP 1st Office Action dated Sep. 15, 2015.
Krissinel and K. Henrick (Sep. 2007) "Inference of macromolecular assemblies from crystalline state," Journal of Molecular Biology, 372(3):774-797.
Larkin et al. (Nov. 2007) "Clustal W and Clustal X version 2.0," Bioinformatics, 23(21):2947-2948.
Lawrence and PM Colman (Dec. 1993) "Shape complementarity at protein/protein interfaces," Journal of Molecular Biology, 234(4):946-950.
Liu et al. (Sep. 2008) "Molecular architecture of native HIV-1 gp120 trimers," Nature, 455(7209):109-113.
Lok et al. (Mar. 2008) "Binding of a neutralizing antibody to dengue virus alters the arrangement of surface glycoproteins," Nature Structural & Molecular Biology, 15(3):312-317.
Lopez et al. (1998) J Virol, 72:6922-6928.
López et al. (Dec. 1993) "Conformational constraints of conserved neutralizing epitopes from a major antigenic area of human respiratory syncytial virus fusion glycoprotein," Journal of General Virology, 74(Pt 12):2567-2577.
McCoy et al. (Aug. 2007) "Phaser crystallographic software," Journal of Applied Crystallography, 40(Pt 4):658-674.
McLellan et al. (Feb. 2010) "Structural basis of respiratory syncytial virus neutralization by motavizumab," Nature Structural & Molecular Biology, 17(2):248-250.
Mejias et al. (Oct. 2007) "Motavizumab, a neutralizing anti-Respiratory Syncytial Virus (Rsv) monoclonal antibody significantly modifies the local and systemic cytokine responses induced by Rsv in the mouse model," Virology Journal, 4:109.
Ofek et al. (Oct. 2010) "Elicitation of structure-specific antibodies by epitope scaffolds," Proceedings of the National Academy of Sciences USA, 107(42):17880-17887.
Otwinowski and W. Minor (1997; retrieved May 2016) "[20] Processing of X-ray diffraction data collected in oscillation mode," Methods in Enzymology, 276:307-326.
Pastor et al. (Dec. 2007) "Resdesign of protein domains using one-bead-one-compound combinatorial chemistry," Journal of the American Chemical Society, 129(48):14922-14932.
Sia et al. (Aug. 2003) "Protein grafting of an HIV-1 inhibiting epitope," Proceedings of the National Academy of Sciences USA, 100(17):9756-9761.
Smith et al. (May 2002) "Modelling the structure of the fusion protein from human respiratory syncytial virus," Protein Engineering, 15(5):365-371.
Tao et al. (Jun. 1997) "Structure of bacteriophage T4 fibritin: a segmented coiled coil and the role of the C-terminal domain," Structure, 5(6):789-798.
The IMpact-RSV Study Group (Sep. 1998) "Palivizumab, a humanized respiratory syncytial virus monoclonal antibody, reduces hospitalization from respiratory syncytial virus infection in high-risk infants," Pediatrics, 102(3):531-537.

(56) References Cited

OTHER PUBLICATIONS

Thompson et al. (Jan. 2003) "Mortality associated with influenza and respiratory syncytial virus in the United States," Journal of the American Medical Association (JAMA), 289(2):179-186.
Wu et al. (Jul. 2005) "Ultra-potent antibodies against respiratory syncytial virus: effects of binding kinetics and binding valence on viral neutralization," Journal of Molecular Biology, 350(1):126-144.
Wu et al. (Oct. 2007) "Characterization of the epitope for anti-human respiratory syncytial virus F protein monoclonal antibody 101F using synthetic peptides and genetic approaches," Journal of General Virology, 88(Pt 10):2719-2723.
Yin et al. (Jan. 2006) "Structure of the parainfluenza virus 5 F protein in its metastable, prefusion conformation," Nature, 439(7072):38-44.
Zhao et al. (Dec. 2004) "Variable resistance to palivizumab in cotton rats by respiratory syncytial virus mutants," Journal of Infectious Diseases, 190(11):1941-1946.

* cited by examiner

```
GSMSDRRKDLEERLDKLLEAAKNKEDKFKAAMRKRGQREERMKDWAKIARDEFEQFRKAV   60  FFL_003
GSMSDARKDLEERLDKLLEAAKNKDKFKAAMRKRGQREERKKDWAKIVRDEFEQFRKAV   60  FFL_004
GSLSDIRKDAERRFDKLVEAVKNKLDKMKAALRKEGQQEERMKDLMKFMRKEVEQLRKAM   60  FFL_007
GSRSDMRKDAERRFDKFVEAAKNKFDKFKAALRKGDIKEERRKDMKKLARKEAEQARRAV   60  FFL_001
GSLSDVRKDVEKRIDKALEAFKNKMDKEKAAFRKDPPSEERRKDKKKEFREEREQVRKAI   60  FFL_002
GSFSDIRKDAEBDRADKAFEAAKNKFDKIKAAIRKDWPSEERAKDLMKKARYEMEQARRAI  60  FFL_006
GSLSDLMKDLEKRFDKFMEAIKNKWDKVKAAFRKQEKGEERAKDMFKIFREELEQLRKAI   60  FFL_008
GSMSDIRKDLEERFDKLVEALKNKVDKMKAAFRKDQFHEERMKDWFKDLRKEVEQMRRAV   60  FFL_005
GSISDIRKDAEVRMDKAVEAFKNKLDKFKQAVRKVFPTEERIKDWLKIVRGEAEQARVAV  60  T93
  *     **   *  *   **  **    *    **   *** *   *  *   *  *

RNFLSEALSKIN------DYPITNDDKKLTSNDAKKFDAEVAKKLEAFKADAEEAATQ----  112  FFL_003
RNFLSEALSKIN------DYPITNDKKLTSNDTKKFAAEVEKKLEAFKADVEEAATQ----  112  FFL_004
RNFLSEALSKIN------DMPITNDDKKLISNDLKKYDAIAEKKLEAMKADVERMATQGSW  115  FFL_007
RNRLSELLSKIN------DMPITNDQKKLMSNDVLKFAAEAEKKIEALAADAEDKFTQGSW  115  FFL_001
RNVLSEALSKIN------DLPITNDKKKLVSNDVIKKVAEMKKKVELEVADVEKKVTQGSW  115  FFL_002
RNIESEALSKIN------DLPITNDQKKLASNDIIKEMARLFKKLEALMADIEILVTQ---  112  FFL_006
RNALSEALSKIN------DLPITNDDKKLASNKAKKRAARVMKKVEAFIADVEAWKTQ---  112  FFL_008
RNYASEALSKIN------DLPITNDDKKLASNDVLKLVAEVWKKLEAILADVEAWFTQ---  112  FFL_005
RNVGRDANDKAAALGKDKEINWFDISQSLWDVQKLTDAAIKKIEAALADMEAWLTQ----  116  T93
 *                   *   *             *
```

Figure 3

SEQUENCE LISTING

```
<160> NUMBER OF SEQ ID NOS: 37

<210> SEQ ID NO 1
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optionally absent
<220> FEATURE:
<221> NAME/KEY: MISC_FEATURE
<222> LOCATION: (3)..(3)
<223> OTHER INFORMATION: X is M, L, R, or F
<220> FEATURE:
<221> NAME/KEY: MISC_FEATURE
<222> LOCATION: (6)..(6)
<223> OTHER INFORMATION: X is R, A, I, M, V or L
<220> FEATURE:
<221> NAME/KEY: MISC_FEATURE
<222> LOCATION: (7)..(7)
<223> OTHER INFORMATION: X is R or M
<220> FEATURE:
<221> NAME/KEY: MISC_FEATURE
<222> LOCATION: (10)..(10)
<223> OTHER INFORMATION: X is L, A, or V
<220> FEATURE:
<221> NAME/KEY: MISC_FEATURE
<222> LOCATION: (12)..(12)
<223> OTHER INFORMATION: X is E, R, K or D
<220> FEATURE:
<221> NAME/KEY: MISC_FEATURE
<222> LOCATION: (14)..(14)
<223> OTHER INFORMATION: X is L, F, I or A
<220> FEATURE:
<221> NAME/KEY: MISC_FEATURE
<222> LOCATION: (17)..(17)
<223> OTHER INFORMATION: X is L, F, or A
<220> FEATURE:
<221> NAME/KEY: MISC_FEATURE
<222> LOCATION: (18)..(18)
<223> OTHER INFORMATION: X is L, V, F, or M
<220> FEATURE:
<221> NAME/KEY: MISC_FEATURE
<222> LOCATION: (21)..(21)
<223> OTHER INFORMATION: X is A, V, F, I or L
<220> FEATURE:
<221> NAME/KEY: MISC_FEATURE
<222> LOCATION: (25)..(25)
<223> OTHER INFORMATION: X is E, M, L, F, W, or V
<220> FEATURE:
```

```
<221> NAME/KEY: MISC_FEATURE
<222> LOCATION: (28)..(28)
<223> OTHER INFORMATION: X is F, M, E, I, or V
<220> FEATURE:
<221> NAME/KEY: MISC_FEATURE
<222> LOCATION: (32)..(32)
<223> OTHER INFORMATION: X is M, L, F, or I
<220> FEATURE:
<221> NAME/KEY: MISC_FEATURE
<222> LOCATION: (35)..(35)
<223> OTHER INFORMATION: X is R, E, G, D, or Q
<220> FEATURE:
<221> NAME/KEY: MISC_FEATURE
<222> LOCATION: (36)..(36)
<223> OTHER INFORMATION: X is G, D, P, W, E, or Q
<220> FEATURE:
<221> NAME/KEY: MISC_FEATURE
<222> LOCATION: (37)..(37)
<223> OTHER INFORMATION: X is Q, I, P, K or F
<220> FEATURE:
<221> NAME/KEY: MISC_FEATURE
<222> LOCATION: (38)..(38)
<223> OTHER INFORMATION: X is R, Q, K, S, G or H
<220> FEATURE:
<221> NAME/KEY: MISC_FEATURE
<222> LOCATION: (42)..(42)
<223> OTHER INFORMATION: X is M, K, R or A
<220> FEATURE:
<221> NAME/KEY: MISC_FEATURE
<222> LOCATION: (45)..(45)
<223> OTHER INFORMATION: X is W, L, K or M
<220> FEATURE:
<221> NAME/KEY: MISC_FEATURE
<222> LOCATION: (46)..(46)
<223> OTHER INFORMATION: X is A, M, K or F
<220> FEATURE:
<221> NAME/KEY: MISC_FEATURE
<222> LOCATION: (48)..(48)
<223> OTHER INFORMATION: X is I, F, L, E, K or D
<220> FEATURE:
<221> NAME/KEY: MISC_FEATURE
<222> LOCATION: (49)..(49)
<223> OTHER INFORMATION: X is A, V, M, F, or L
<220> FEATURE:
<221> NAME/KEY: MISC_FEATURE
<222> LOCATION: (51)..(51)
<223> OTHER INFORMATION: X is D, K, E, or Y
<220> FEATURE:
<221> NAME/KEY: MISC_FEATURE
<222> LOCATION: (53)..(53)
<223> OTHER INFORMATION: X is F, V, A, R, M or L
<220> FEATURE:
<221> NAME/KEY: MISC_FEATURE
<222> LOCATION: (56)..(56)
<223> OTHER INFORMATION: X is F, L, A, V or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, V, I, A, or Y
<220> FEATURE:
<221> NAME/KEY: MISC_FEATURE
<222> LOCATION: (64)..(64)
<223> OTHER INFORMATION: X is L,  E, or  A
<220> FEATURE:
<221> NAME/KEY: MISC_FEATURE
<222> LOCATION: (67)..(67)
<223> OTHER INFORMATION: X is A or L
<220> FEATURE:
<221> NAME/KEY: MISC_FEATURE
<222> LOCATION: (72)..(72)
<223> OTHER INFORMATION: X is N or Y
```

-continued

```
<220> FEATURE:
<221> NAME/KEY: MISC_FEATURE
<222> LOCATION: (74)..(74)
<223> OTHER INFORMATION: X is Y, M or L
<220> FEATURE:
<221> NAME/KEY: MISC_FEATURE
<222> LOCATION: (78)..(78)
<223> OTHER INFORMATION: X is N or I
<220> FEATURE:
<221> NAME/KEY: MISC_FEATURE
<222> LOCATION: (80)..(80)
<223> OTHER INFORMATION: X is D, Q, or K
<220> FEATURE:
<221> NAME/KEY: MISC_FEATURE
<222> LOCATION: (82)..(82)
<223> OTHER INFORMATION: X is K, E, T, M or Q
<220> FEATURE:
<221> NAME/KEY: MISC_FEATURE
<222> LOCATION: (84)..(84)
<223> OTHER INFORMATION: X is T, I, M, V or A
<220> FEATURE:
<221> NAME/KEY: MISC_FEATURE
<222> LOCATION: (87)..(87)
<223> OTHER INFORMATION: X is D or K
<220> FEATURE:
<221> NAME/KEY: MISC_FEATURE
<222> LOCATION: (88)..(88)
<223> OTHER INFORMATION: X is A, T, L, V or I
<220> FEATURE:
<221> NAME/KEY: MISC_FEATURE
<222> LOCATION: (89)..(89)
<223> OTHER INFORMATION: X is K, L or I
<220> FEATURE:
<221> NAME/KEY: MISC_FEATURE
<222> LOCATION: (91)..(91)
<223> OTHER INFORMATION: X is F, Y, K, E, R, or L
<220> FEATURE:
<221> NAME/KEY: MISC_FEATURE
<222> LOCATION: (92)..(92)
<223> OTHER INFORMATION: X is D, A, V, or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A, M or L
<220> FEATURE:
<221> NAME/KEY: MISC_FEATURE
<222> LOCATION: (96)..(96)
<223> OTHER INFORMATION: X is A, E, K, F or M
<220> FEATURE:
<221> NAME/KEY: MISC_FEATURE
<222> LOCATION: (99)..(99)
<223> OTHER INFORMATION: X is L, I or V
<220> FEATURE:
<221> NAME/KEY: MISC_FEATURE
<222> LOCATION: (101)..(101)
<223> OTHER INFORMATION: X is A or L
<220> FEATURE:
<221> NAME/KEY: MISC_FEATURE
<222> LOCATION: (102)..(102)
<223> OTHER INFORMATION: X is F, M, L, E or I
<220> FEATURE:
<221> NAME/KEY: MISC_FEATURE
<222> LOCATION: (103)..(103)
<223> OTHER INFORMATION: X is K, A, V, M, I or L
<220> FEATURE:
<221> NAME/KEY: MISC_FEATURE
<222> LOCATION: (106)..(106)
<223> OTHER INFORMATION: X is A, V, or I
<220> FEATURE:
<221> NAME/KEY: MISC_FEATURE
<222> LOCATION: (108)..(108)
<223> OTHER INFORMATION: X is E, R, D, K, I or A
<220> FEATURE:
<221> NAME/KEY: MISC_FEATURE
<222> LOCATION: (109)..(109)
```

```
<223> OTHER INFORMATION: X is A, M, K, L or W
<220> FEATURE:
<221> NAME/KEY: MISC_FEATURE
<222> LOCATION: (110)..(110)
<223> OTHER INFORMATION: X is A, F, V, or K
<220> FEATURE:
<221> NAME/KEY: MISC_FEATURE
<222> LOCATION: (113)..(115)
<223> OTHER INFORMATION: optionally absent

<400> SEQUENCE: 1

Gly Ser Xaa Ser Asp Xaa Xaa Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
            35                  40                  45

Xaa Arg Xaa Glu Xaa Glu Gln Xaa Arg Xaa Ala Xaa Arg Asn Xaa Xaa
        50                  55                  60

Ser Glu Xaa Leu Ser Lys Ile Xaa Asp Xaa Pro Ile Thr Xaa Asp Xaa
65                  70                  75                  80

Lys Xaa Leu Xaa Ser Asn Xaa Xaa Xaa Lys Xaa Xaa Ala Xaa Xaa Xaa
            85                  90                  95

Lys Lys Xaa Glu Xaa Xaa Xaa Ala Asp Xaa Glu Xaa Xaa Xaa Thr Gln
            100                 105                 110

Gly Ser Trp
        115

<210> SEQ ID NO 2
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optionally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is R, A, I, M of V
<220> FEATURE:
<221> NAME/KEY: MISC_FEATURE
<222> LOCATION: (10)..(10)
<223> OTHER INFORMATION: X is L, A, of V
<220> FEATURE:
<221> NAME/KEY: MISC_FEATURE
<222> LOCATION: (12)..(12)
<223> OTHER INFORMATION: X is E, R, K or D
<220> FEATURE:
<221> NAME/KEY: MISC_FEATURE
<222> LOCATION: (14)..(14)
<223> OTHER INFORMATION: X is L, F, I or A
<220> FEATURE:
<221> NAME/KEY: MISC_FEATURE
<222> LOCATION: (17)..(17)
<223> OTHER INFORMATION: X is L, F, or A
<220> FEATURE:
<221> NAME/KEY: MISC_FEATURE
<222> LOCATION: (18)..(18)
<223> OTHER INFORMATION: X is L, V, or F
<220> FEATURE:
<221> NAME/KEY: MISC_FEATURE
<222> LOCATION: (21)..(21)
<223> OTHER INFORMATION: X is A, V, F, or L
```

-continued

```
<220> FEATURE:
<221> NAME/KEY: MISC_FEATURE
<222> LOCATION: (25)..(25)
<223> OTHER INFORMATION: X is M, L, F or V
<220> FEATURE:
<221> NAME/KEY: MISC_FEATURE
<222> LOCATION: (28)..(28)
<223> OTHER INFORMATION: X is F, M, E or I
<220> FEATURE:
<221> NAME/KEY: MISC_FEATURE
<222> LOCATION: (32)..(32)
<223> OTHER INFORMATION: X is M, L, F or I
<220> FEATURE:
<221> NAME/KEY: MISC_FEATURE
<222> LOCATION: (35)..(35)
<223> OTHER INFORMATION: X is R, E, G or D
<220> FEATURE:
<221> NAME/KEY: MISC_FEATURE
<222> LOCATION: (36)..(36)
<223> OTHER INFORMATION: X is G, D, P, W, or Q
<220> FEATURE:
<221> NAME/KEY: MISC_FEATURE
<222> LOCATION: (37)..(37)
<223> OTHER INFORMATION: X is Q, I, P, or F
<220> FEATURE:
<221> NAME/KEY: MISC_FEATURE
<222> LOCATION: (38)..(38)
<223> OTHER INFORMATION: X is R, Q, K, S or H
<220> FEATURE:
<221> NAME/KEY: MISC_FEATURE
<222> LOCATION: (42)..(42)
<223> OTHER INFORMATION: X is M, K, R or A
<220> FEATURE:
<221> NAME/KEY: MISC_FEATURE
<222> LOCATION: (45)..(45)
<223> OTHER INFORMATION: X is W, L, M, or K
<220> FEATURE:
<221> NAME/KEY: MISC_FEATURE
<222> LOCATION: (46)..(46)
<223> OTHER INFORMATION: X is A, M, K or F
<220> FEATURE:
<221> NAME/KEY: MISC_FEATURE
<222> LOCATION: (48)..(48)
<223> OTHER INFORMATION: X is I, F, L, E, K or D
<220> FEATURE:
<221> NAME/KEY: MISC_FEATURE
<222> LOCATION: (49)..(49)
<223> OTHER INFORMATION: X is A, V, M, F or L
<220> FEATURE:
<221> NAME/KEY: MISC_FEATURE
<222> LOCATION: (51)..(51)
<223> OTHER INFORMATION: X is D, K, Y or E
<220> FEATURE:
<221> NAME/KEY: MISC_FEATURE
<222> LOCATION: (53)..(53)
<223> OTHER INFORMATION: X is F, V, A, R, or M
<220> FEATURE:
<221> NAME/KEY: MISC_FEATURE
<222> LOCATION: (56)..(56)
<223> OTHER INFORMATION: X is F, L, V, A, or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, V, I or Y
<220> FEATURE:
<221> NAME/KEY: MISC_FEATURE
<222> LOCATION: (64)..(64)
<223> OTHER INFORMATION: X is L, E or A
<220> FEATURE:
<221> NAME/KEY: MISC_FEATURE
<222> LOCATION: (67)..(67)
```

```
<223> OTHER INFORMATION: X is A or L
<220> FEATURE:
<221> NAME/KEY: MISC_FEATURE
<222> LOCATION: (74)..(74)
<223> OTHER INFORMATION: X is Y, M, or L
<220> FEATURE:
<221> NAME/KEY: MISC_FEATURE
<222> LOCATION: (80)..(80)
<223> OTHER INFORMATION: X is D, Q or K
<220> FEATURE:
<221> NAME/KEY: MISC_FEATURE
<222> LOCATION: (84)..(84)
<223> OTHER INFORMATION: X is T, I, M, V, or A
<220> FEATURE:
<221> NAME/KEY: MISC_FEATURE
<222> LOCATION: (88)..(88)
<223> OTHER INFORMATION: X is T, L, V or I
<220> FEATURE:
<221> NAME/KEY: MISC_FEATURE
<222> LOCATION: (89)..(89)
<223> OTHER INFORMATION: X is K, L, or I
<220> FEATURE:
<221> NAME/KEY: MISC_FEATURE
<222> LOCATION: (91)..(91)
<223> OTHER INFORMATION: X is F, Y, K, E or L
<220> FEATURE:
<221> NAME/KEY: MISC_FEATURE
<222> LOCATION: (92)..(92)
<223> OTHER INFORMATION: X is D, A, V or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A, M or L
<220> FEATURE:
<221> NAME/KEY: MISC_FEATURE
<222> LOCATION: (96)..(96)
<223> OTHER INFORMATION: X is E, K, F or W
<220> FEATURE:
<221> NAME/KEY: MISC_FEATURE
<222> LOCATION: (99)..(99)
<223> OTHER INFORMATION: X is L, I or V
<220> FEATURE:
<221> NAME/KEY: MISC_FEATURE
<222> LOCATION: (101)..(101)
<223> OTHER INFORMATION: X is A or L
<220> FEATURE:
<221> NAME/KEY: MISC_FEATURE
<222> LOCATION: (102)..(102)
<223> OTHER INFORMATION: X is F, M, L, E or I
<220> FEATURE:
<221> NAME/KEY: MISC_FEATURE
<222> LOCATION: (103)..(103)
<223> OTHER INFORMATION: X is K, A, V, M, or L
<220> FEATURE:
<221> NAME/KEY: MISC_FEATURE
<222> LOCATION: (106)..(106)
<223> OTHER INFORMATION: X is A, V or I
<220> FEATURE:
<221> NAME/KEY: MISC_FEATURE
<222> LOCATION: (108)..(108)
<223> OTHER INFORMATION: X is E, R, D, K, I or A
<220> FEATURE:
<221> NAME/KEY: MISC_FEATURE
<222> LOCATION: (109)..(109)
<223> OTHER INFORMATION: X is A, M, K, L or W
<220> FEATURE:
<221> NAME/KEY: MISC_FEATURE
<222> LOCATION: (110)..(110)
<223> OTHER INFORMATION: X is A, F or V
<220> FEATURE:
<221> NAME/KEY: MISC_FEATURE
<222> LOCATION: (113)..(115)
<223> OTHER INFORMATION: optionally absent

<400> SEQUENCE: 2
```

```
Gly Ser Xaa Ser Asp Xaa Arg Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
            35                  40                  45

Xaa Arg Xaa Glu Xaa Glu Gln Xaa Arg Xaa Ala Xaa Arg Asn Xaa Xaa
        50                  55                  60

Ser Glu Xaa Leu Ser Lys Ile Asn Asp Xaa Pro Ile Thr Asn Asp Xaa
65                  70                  75                  80

Lys Lys Leu Xaa Ser Asn Asp Xaa Xaa Lys Xaa Xaa Ala Xaa Xaa Xaa
            85                  90                  95

Lys Lys Xaa Glu Xaa Xaa Xaa Ala Asp Xaa Glu Xaa Xaa Xaa Thr Gln
            100                 105                 110

Gly Ser Trp
        115

<210> SEQ ID NO 3
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optionally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is I or M
<220> FEATURE:
<221> NAME/KEY: MISC_FEATURE
<222> LOCATION: (10)..(10)
<223> OTHER INFORMATION: X is L or A
<220> FEATURE:
<221> NAME/KEY: MISC_FEATURE
<222> LOCATION: (12)..(12)
<223> OTHER INFORMATION: X is E, R or D
<220> FEATURE:
<221> NAME/KEY: MISC_FEATURE
<222> LOCATION: (14)..(14)
<223> OTHER INFORMATION: X is F or A
<220> FEATURE:
<221> NAME/KEY: MISC_FEATURE
<222> LOCATION: (17)..(17)
<223> OTHER INFORMATION: X is L, F or A
<220> FEATURE:
<221> NAME/KEY: MISC_FEATURE
<222> LOCATION: (18)..(18)
<223> OTHER INFORMATION: X is V or F
<220> FEATURE:
<221> NAME/KEY: MISC_FEATURE
<222> LOCATION: (21)..(21)
<223> OTHER INFORMATION: X is A, V or L
<220> FEATURE:
<221> NAME/KEY: MISC_FEATURE
<222> LOCATION: (25)..(25)
<223> OTHER INFORMATION: X is L, F, or W
<220> FEATURE:
<221> NAME/KEY: MISC_FEATURE
<222> LOCATION: (28)..(28)
<223> OTHER INFORMATION: X is M, F, or I
<220> FEATURE:
<221> NAME/KEY: MISC_FEATURE
<222> LOCATION: (32)..(32)
```

```
<223> OTHER INFORMATION: X is L, F, or I
<220> FEATURE:
<221> NAME/KEY: MISC_FEATURE
<222> LOCATION: (35)..(35)
<223> OTHER INFORMATION: X is E, G, or D
<220> FEATURE:
<221> NAME/KEY: MISC_FEATURE
<222> LOCATION: (36)..(36)
<223> OTHER INFORMATION: X is W, Q,  G, or D
<220> FEATURE:
<221> NAME/KEY: MISC_FEATURE
<222> LOCATION: (37)..(37)
<223> OTHER INFORMATION: X is Q,  I, P, or F
<220> FEATURE:
<221> NAME/KEY: MISC_FEATURE
<222> LOCATION: (38)..(38)
<223> OTHER INFORMATION: X is Q,  K, S, or H
<220> FEATURE:
<221> NAME/KEY: MISC_FEATURE
<222> LOCATION: (42)..(42)
<223> OTHER INFORMATION: X is M, R, or A
<220> FEATURE:
<221> NAME/KEY: MISC_FEATURE
<222> LOCATION: (45)..(45)
<223> OTHER INFORMATION: X is W, L, or M
<220> FEATURE:
<221> NAME/KEY: MISC_FEATURE
<222> LOCATION: (46)..(46)
<223> OTHER INFORMATION: X is M, K or F
<220> FEATURE:
<221> NAME/KEY: MISC_FEATURE
<222> LOCATION: (48)..(48)
<223> OTHER INFORMATION: X is D, L, K or F
<220> FEATURE:
<221> NAME/KEY: MISC_FEATURE
<222> LOCATION: (49)..(49)
<223> OTHER INFORMATION: X is A, M, or L
<220> FEATURE:
<221> NAME/KEY: MISC_FEATURE
<222> LOCATION: (51)..(51)
<223> OTHER INFORMATION: X is Y or K
<220> FEATURE:
<221> NAME/KEY: MISC_FEATURE
<222> LOCATION: (53)..(53)
<223> OTHER INFORMATION: X is V, A or M
<220> FEATURE:
<221> NAME/KEY: MISC_FEATURE
<222> LOCATION: (56)..(56)
<223> OTHER INFORMATION: X is L, A or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, I or Y
<220> FEATURE:
<221> NAME/KEY: MISC_FEATURE
<222> LOCATION: (64)..(64)
<223> OTHER INFORMATION: X is L, E, or A
<220> FEATURE:
<221> NAME/KEY: MISC_FEATURE
<222> LOCATION: (67)..(67)
<223> OTHER INFORMATION: X is L or A
<220> FEATURE:
<221> NAME/KEY: MISC_FEATURE
<222> LOCATION: (72)..(72)
<223> OTHER INFORMATION: X is N or Y
<220> FEATURE:
<221> NAME/KEY: MISC_FEATURE
<222> LOCATION: (74)..(74)
<223> OTHER INFORMATION: X is M or L
<220> FEATURE:
<221> NAME/KEY: MISC_FEATURE
```

```
<222> LOCATION: (78)..(78)
<223> OTHER INFORMATION: X is N or I
<220> FEATURE:
<221> NAME/KEY: MISC_FEATURE
<222> LOCATION: (80)..(80)
<223> OTHER INFORMATION: X is D or Q
<220> FEATURE:
<221> NAME/KEY: MISC_FEATURE
<222> LOCATION: (82)..(82)
<223> OTHER INFORMATION: X is K, E, T, M, or Q
<220> FEATURE:
<221> NAME/KEY: MISC_FEATURE
<222> LOCATION: (84)..(84)
<223> OTHER INFORMATION: X is I, M, or A
<220> FEATURE:
<221> NAME/KEY: MISC_FEATURE
<222> LOCATION: (88)..(88)
<223> OTHER INFORMATION: X is I, L, or V
<220> FEATURE:
<221> NAME/KEY: MISC_FEATURE
<222> LOCATION: (89)..(89)
<223> OTHER INFORMATION: X is I, L, or K
<220> FEATURE:
<221> NAME/KEY: MISC_FEATURE
<222> LOCATION: (91)..(91)
<223> OTHER INFORMATION: X is F, Y, E or L
<220> FEATURE:
<221> NAME/KEY: MISC_FEATURE
<222> LOCATION: (92)..(92)
<223> OTHER INFORMATION: X is D, A, V, or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A, or L
<220> FEATURE:
<221> NAME/KEY: MISC_FEATURE
<222> LOCATION: (96)..(96)
<223> OTHER INFORMATION: X is E, F or W
<220> FEATURE:
<221> NAME/KEY: MISC_FEATURE
<222> LOCATION: (99)..(99)
<223> OTHER INFORMATION: X is L or I
<220> FEATURE:
<221> NAME/KEY: MISC_FEATURE
<222> LOCATION: (102)..(102)
<223> OTHER INFORMATION: X is M, L or I
<220> FEATURE:
<221> NAME/KEY: MISC_FEATURE
<222> LOCATION: (103)..(103)
<223> OTHER INFORMATION: X is K, A, M, or L
<220> FEATURE:
<221> NAME/KEY: MISC_FEATURE
<222> LOCATION: (106)..(106)
<223> OTHER INFORMATION: X is  A, V, or I
<220> FEATURE:
<221> NAME/KEY: MISC_FEATURE
<222> LOCATION: (108)..(108)
<223> OTHER INFORMATION: X is R, D, I or A
<220> FEATURE:
<221> NAME/KEY: MISC_FEATURE
<222> LOCATION: (109)..(109)
<223> OTHER INFORMATION: X is M, K, L or W
<220> FEATURE:
<221> NAME/KEY: MISC_FEATURE
<222> LOCATION: (110)..(110)
<223> OTHER INFORMATION: X is A, F, or V
<220> FEATURE:
<221> NAME/KEY: MISC_FEATURE
<222> LOCATION: (113)..(115)
<223> OTHER INFORMATION: optionally absent

<400> SEQUENCE: 3

Gly Ser Xaa Ser Asp Xaa Arg Lys Asp Xaa Glu Xaa Arg Xaa Asp Lys
1               5                   10                  15
```

```
Xaa Xaa Glu Ala Xaa Lys Asn Lys Xaa Asp Lys Xaa Lys Ala Ala Xaa
            20                  25                  30

Arg Lys Xaa Xaa Xaa Glu Glu Arg Xaa Lys Asp Xaa Xaa Lys Xaa
        35                  40                  45

Xaa Arg Xaa Glu Xaa Gln Xaa Arg Xaa Ala Xaa Arg Asn Xaa Xaa
    50                  55                  60

Ser Glu Xaa Leu Ser Lys Ile Xaa Asp Xaa Pro Ile Thr Xaa Asp Xaa
65                  70                  75                  80

Lys Xaa Leu Xaa Ser Asn Asp Xaa Xaa Lys Xaa Xaa Ala Xaa Xaa Xaa
                85                  90                  95

Lys Lys Xaa Glu Ala Xaa Xaa Ala Asp Xaa Glu Xaa Xaa Xaa Thr Gln
            100                 105                 110

Gly Ser Trp
        115

<210> SEQ ID NO 4
<211> LENGTH: 115
<212> TYPE: PRT
<213> ORGANISM: Artificial Sequence
<220> FEATURE:
<223> OTHER INFORMATION: Synthetic

<400> SEQUENCE: 4

Gly Ser Arg Ser Asp Met Arg Lys Asp Ala Glu Arg Arg Phe Asp Lys
1               5                   10                  15

Phe Val Glu Ala Ala Lys Asn Lys Phe Asp Lys Phe Lys Ala Ala Leu
            20                  25                  30

Arg Lys Gly Asp Ile Lys Glu Glu Arg Arg Lys Asp Met Lys Lys Leu
        35                  40                  45

Ala Arg Lys Glu Ala Glu Gln Ala Arg Arg Ala Val Arg Asn Arg Leu
    50                  55                  60

Ser Glu Leu Leu Ser Lys Ile Asn Asp Met Pro Ile Thr Asn Asp Gln
65                  70                  75                  80

Lys Lys Leu Met Ser Asn Asp Val Leu Lys Phe Ala Ala Glu Ala Glu
                85                  90                  95

Lys Lys Ile Glu Ala Leu Ala Ala Asp Ala Glu Asp Lys Phe Thr Gln
            100                 105                 110

Gly Ser Trp
        115

<210> SEQ ID NO 5
<211> LENGTH: 115
<212> TYPE: PRT
<213> ORGANISM: Artificial Sequence
<220> FEATURE:
<223> OTHER INFORMATION: Synthetic

<400> SEQUENCE: 5

Gly Ser Leu Ser Asp Val Arg Lys Asp Val Glu Lys Arg Ile Asp Lys
1               5                   10                  15

Ala Leu Glu Ala Phe Lys Asn Lys Met Asp Lys Glu Lys Ala Ala Phe
            20                  25                  30

Arg Lys Asp Pro Pro Ser Glu Arg Arg Lys Asp Lys Lys Lys Glu
        35                  40                  45

Phe Arg Glu Glu Arg Glu Gln Val Arg Lys Ala Ile Arg Asn Val Leu
    50                  55                  60

Ser Glu Ala Leu Ser Lys Ile Asn Asp Leu Pro Ile Thr Asn Asp Lys
```

```
                65                  70                  75                  80
Lys Lys Leu Val Ser Asn Asp Val Ile Lys Val Ala Glu Met Lys
                    85                  90                  95

Lys Lys Val Glu Leu Glu Val Ala Asp Val Glu Lys Lys Val Thr Gln
                100                 105                 110

Gly Ser Trp
        115

<210> SEQ ID NO 6
<211> LENGTH: 112
<212> TYPE: PRT
<213> ORGANISM: Artificial Sequence
<220> FEATURE:
<223> OTHER INFORMATION: Synthetic

<400> SEQUENCE: 6

Gly Ser Met Ser Asp Ala Arg Lys Asp Leu Glu Arg Leu Asp Lys
1               5                   10                  15

Leu Leu Glu Ala Ala Lys Asn Lys Met Asp Lys Phe Lys Ala Ala Met
                    20                  25                  30

Arg Lys Arg Gly Gln Arg Glu Glu Arg Lys Lys Asp Trp Ala Lys Ile
                35                  40                  45

Val Arg Asp Glu Phe Glu Gln Phe Arg Lys Ala Val Arg Asn Phe Leu
            50                  55                  60

Ser Glu Ala Leu Ser Lys Ile Asn Asp Tyr Pro Ile Thr Asn Asp Asp
65                  70                  75                  80

Lys Lys Leu Thr Ser Asn Asp Thr Lys Lys Phe Ala Ala Glu Val Glu
                    85                  90                  95

Lys Lys Leu Glu Ala Phe Lys Ala Asp Val Glu Glu Ala Ala Thr Gln
                100                 105                 110

<210> SEQ ID NO 7
<211> LENGTH: 112
<212> TYPE: PRT
<213> ORGANISM: Artificial Sequence
<220> FEATURE:
<223> OTHER INFORMATION: Synthetic

<400> SEQUENCE: 7

Gly Ser Met Ser Asp Ile Arg Lys Asp Leu Glu Glu Arg Phe Asp Lys
1               5                   10                  15

Leu Val Glu Ala Leu Lys Asn Lys Val Asp Lys Met Lys Ala Ala Phe
                    20                  25                  30

Arg Lys Asp Gln Phe His Glu Glu Arg Met Lys Asp Trp Phe Lys Asp
                35                  40                  45

Leu Arg Lys Glu Val Gln Met Arg Arg Ala Val Arg Asn Tyr Ala
            50                  55                  60

Ser Glu Ala Leu Ser Lys Ile Asn Asp Leu Pro Ile Thr Asn Asp Asp
65                  70                  75                  80

Lys Lys Leu Ala Ser Asn Asp Val Leu Lys Leu Val Ala Glu Val Trp
                    85                  90                  95

Lys Lys Leu Glu Ala Ile Leu Ala Asp Val Glu Ala Trp Phe Thr Gln
                100                 105                 110

<210> SEQ ID NO 8
<211> LENGTH: 112
<212> TYPE: PRT
<213> ORGANISM: Artificial Sequence
<220> FEATURE:
```

<223> OTHER INFORMATION: Synthetic

<400> SEQUENCE: 8

```
Gly Ser Phe Ser Asp Ile Arg Lys Asp Ala Glu Asp Arg Ala Asp Lys
1               5                   10                  15

Ala Phe Glu Ala Ala Lys Asn Lys Phe Asp Lys Ile Lys Ala Ala Ile
            20                  25                  30

Arg Lys Asp Trp Pro Ser Glu Glu Arg Ala Lys Asp Leu Met Lys Lys
        35                  40                  45

Ala Arg Tyr Glu Met Glu Gln Ala Arg Arg Ala Ile Arg Asn Ile Glu
    50                  55                  60

Ser Glu Ala Leu Ser Lys Ile Asn Asp Leu Pro Ile Thr Asn Asp Gln
65                  70                  75                  80

Lys Lys Leu Ala Ser Asn Asp Ile Ile Lys Glu Met Ala Arg Leu Phe
                85                  90                  95

Lys Lys Leu Glu Ala Leu Met Ala Asp Ile Glu Ile Leu Val Thr Gln
            100                 105                 110
```

<210> SEQ ID NO 9
<211> LENGTH: 115
<212> TYPE: PRT
<213> ORGANISM: Artificial Sequence
<220> FEATURE:
<223> OTHER INFORMATION: Synthetic

<400> SEQUENCE: 9

```
Gly Ser Leu Ser Asp Ile Arg Lys Asp Ala Glu Arg Arg Phe Asp Lys
1               5                   10                  15

Leu Val Glu Ala Val Lys Asn Lys Leu Asp Lys Met Lys Ala Ala Leu
            20                  25                  30

Arg Lys Glu Gly Gln Gln Glu Arg Met Lys Asp Leu Met Lys Phe
        35                  40                  45

Met Arg Lys Glu Val Gly Gln Leu Arg Lys Ala Met Arg Asn Phe Leu
    50                  55                  60

Ser Glu Ala Leu Ser Lys Ile Asn Asp Met Pro Ile Thr Asn Asp Asp
65                  70                  75                  80

Lys Lys Leu Ile Ser Asn Asp Leu Lys Lys Tyr Asp Ala Ile Ala Glu
                85                  90                  95

Lys Lys Leu Glu Ala Met Lys Ala Asp Val Gly Arg Met Ala Thr Gln
            100                 105                 110

Gly Ser Trp
        115
```

<210> SEQ ID NO 10
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (82)..(82)
<223> OTHER INFORMATION: X is E, T, M, or Q

<400> SEQUENCE: 10

```
Gly Ser Arg Ser Asp Met Arg Lys Asp Ala Glu Arg Arg Phe Asp Lys
1               5                   10                  15

Phe Val Glu Ala Ala Lys Asn Lys Phe Asp Lys Phe Lys Ala Ala Leu
            20                  25                  30
```

-continued

```
Arg Lys Gly Asp Ile Lys Glu Glu Arg Arg Lys Asp Met Lys Lys Leu
            35                  40                  45

Ala Arg Lys Glu Ala Gly Gln Ala Arg Ala Val Arg Asn Arg Leu
 50                  55                  60

Ser Glu Leu Leu Ser Lys Ile Asn Asp Met Pro Ile Thr Asn Asp Gln
 65                  70                  75                  80

Lys Xaa Leu Met Ser Asn Asp Val Leu Lys Phe Ala Ala Glu Ala Glu
                 85                  90                  95

Lys Lys Ile Glu Ala Leu Ala Ala Asp Ala Glu Asp Lys Phe Thr Gln
            100                 105                 110

Gly Ser Trp
        115
```

<210> SEQ ID NO 11
<211> LENGTH: 112
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (82)..(82)
<223> OTHER INFORMATION: X is E, T, M, or Q

<400> SEQUENCE: 11

```
Gly Ser Met Ser Asp Ile Arg Lys Asp Leu Glu Glu Arg Phe Asp Lys
 1               5                  10                  15

Leu Val Glu Ala Leu Lys Asn Lys Val Asp Lys Met Lys Ala Ala Phe
                20                  25                  30

Arg Lys Asp Gln Phe His Glu Glu Arg Met Lys Asp Trp Phe Lys Asp
            35                  40                  45

Leu Arg Lys Glu Val Glu Gln Met Arg Arg Ala Val Arg Asn Tyr Ala
 50                  55                  60

Ser Glu Ala Leu Ser Lys Ile Asn Asp Leu Pro Ile Thr Asn Asp Asp
 65                  70                  75                  80

Lys Xaa Leu Ala Ser Asn Asp Val Leu Lys Leu Val Ala Glu Val Trp
                 85                  90                  95

Lys Lys Leu Glu Ala Ile Leu Ala Asp Val Glu Ala Trp Phe Thr Gln
            100                 105                 110
```

<210> SEQ ID NO 12
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (82)..(82)
<223> OTHER INFORMATION: X is E, T, M, or Q

<400> SEQUENCE: 12

```
Gly Ser Leu Ser Asp Ile Arg Lys Asp Ala Glu Arg Arg Phe Asp Lys
 1               5                  10                  15

Leu Val Glu Ala Val Lys Asn Lys Leu Asp Lys Met Lys Ala Ala Leu
                20                  25                  30

Arg Lys Glu Gly Gln Gln Glu Glu Arg Met Lys Asp Leu Met Lys Phe
            35                  40                  45

Met Arg Lys Glu Val Glu Gln Leu Arg Lys Ala Met Arg Asn Phe Leu
 50                  55                  60
```

```
Ser Glu Ala Leu Ser Lys Ile Asn Asp Met Pro Ile Thr Asn Asp Asp
 65                  70                  75                  80

Lys Xaa Leu Ile Ser Asn Asp Leu Lys Lys Tyr Asp Ala Ile Ala Glu
                 85                  90                  95

Lys Lys Leu Glu Ala Met Lys Ala Asp Val Glu Arg Met Ala Thr Gln
            100                 105                 110

Gly Ser Trp
        115

<210> SEQ ID NO 13
<211> LENGTH: 115
<212> TYPE: PRT
<213> ORGANISM: Artificial Sequence
<220> FEATURE:
<223> OTHER INFORMATION: Synthetic

<400> SEQUENCE: 13

Gly Ser Arg Ser Asp Met Arg Lys Asp Ala Glu Arg Arg Phe Asp Lys
 1               5                   10                  15

Phe Val Glu Ala Ala Lys Asn Lys Phe Asp Lys Phe Lys Ala Ala Leu
                20                  25                  30

Arg Lys Gly Asp Ile Lys Glu Glu Arg Lys Asp Met Lys Lys Leu
            35                  40                  45

Ala Arg Lys Glu Ala Glu Gln Ala Arg Arg Ala Val Arg Asn Arg Leu
         50                  55                  60

Ser Glu Leu Leu Ser Lys Ile Tyr Asp Met Pro Ile Thr Asn Asp Gln
 65                  70                  75                  80

Lys Lys Leu Met Ser Asn Asp Val Leu Lys Phe Ala Ala Glu Ala Glu
                 85                  90                  95

Lys Lys Ile Glu Ala Leu Ala Ala Asp Ala Glu Asp Lys Phe Thr Gln
            100                 105                 110

Gly Ser Trp
        115

<210> SEQ ID NO 14
<211> LENGTH: 112
<212> TYPE: PRT
<213> ORGANISM: Artificial Sequence
<220> FEATURE:
<223> OTHER INFORMATION: Synthetic

<400> SEQUENCE: 14

Gly Ser Met Ser Asp Ile Arg Lys Asp Leu Glu Glu Arg Phe Asp Lys
 1               5                   10                  15

Leu Val Glu Ala Leu Lys Asn Lys Val Asp Lys Met Lys Ala Ala Phe
                20                  25                  30

Arg Lys Asp Gln Phe His Glu Arg Met Lys Asp Trp Phe Lys Asp
            35                  40                  45

Leu Arg Lys Glu Val Glu Gln Met Arg Arg Ala Val Arg Asn Tyr Ala
         50                  55                  60

Ser Glu Ala Leu Ser Lys Ile Tyr Asp Leu Pro Ile Thr Asn Asp Asp
 65                  70                  75                  80

Lys Lys Leu Ala Ser Asn Asp Val Leu Lys Leu Val Ala Glu Val Trp
                 85                  90                  95

Lys Lys Leu Glu Ala Ile Leu Ala Asp Val Glu Ala Trp Phe Thr Gln
            100                 105                 110

<210> SEQ ID NO 15
```

```
<211> LENGTH: 115
<212> TYPE: PRT
<213> ORGANISM: Artificial Sequence
<220> FEATURE:
<223> OTHER INFORMATION: Synthetic

<400> SEQUENCE: 15

Gly Ser Leu Ser Asp Ile Arg Lys Asp Ala Glu Arg Phe Asp Lys
1               5                   10                  15

Leu Val Glu Ala Val Lys Asn Lys Leu Asp Lys Met Lys Ala Ala Leu
            20                  25                  30

Arg Lys Glu Gly Gln Gln Glu Glu Arg Met Lys Asp Leu Met Lys Phe
        35                  40                  45

Met Arg Lys Glu Val Glu Gln Leu Arg Lys Ala Met Arg Asn Phe Leu
    50                  55                  60

Ser Glu Ala Leu Ser Lys Ile Tyr Asp Met Pro Ile Thr Asn Asp Asp
65                  70                  75                  80

Lys Lys Leu Ile Ser Asn Asp Leu Lys Lys Tyr Asp Ala Ile Ala Glu
                85                  90                  95

Lys Lys Leu Glu Ala Met Lys Ala Asp Val Glu Arg Met Ala Thr Gln
            100                 105                 110

Gly Ser Trp
        115

<210> SEQ ID NO 16
<211> LENGTH: 115
<212> TYPE: PRT
<213> ORGANISM: Artificial Sequence
<220> FEATURE:
<223> OTHER INFORMATION: Synthetic

<400> SEQUENCE: 16

Gly Ser Arg Ser Asp Met Arg Lys Asp Ala Glu Arg Phe Asp Lys
1               5                   10                  15

Phe Val Glu Ala Ala Lys Asn Lys Phe Asp Lys Phe Lys Ala Ala Leu
            20                  25                  30

Arg Lys Gly Asp Ile Lys Glu Glu Arg Arg Lys Asp Met Lys Lys Leu
        35                  40                  45

Ala Arg Lys Glu Ala Glu Gln Ala Arg Ala Val Arg Asn Arg Leu
    50                  55                  60

Ser Glu Leu Leu Ser Lys Ile Asn Asp Met Pro Ile Thr Ile Asp Gln
65                  70                  75                  80

Lys Lys Leu Met Ser Asn Asp Val Leu Lys Phe Ala Ala Glu Ala Glu
                85                  90                  95

Lys Lys Ile Glu Ala Leu Ala Ala Asp Ala Glu Asp Lys Phe Thr Gln
            100                 105                 110

Gly Ser Trp
        115

<210> SEQ ID NO 17
<211> LENGTH: 112
<212> TYPE: PRT
<213> ORGANISM: Artificial Sequence
<220> FEATURE:
<223> OTHER INFORMATION: Synthetic

<400> SEQUENCE: 17

Gly Ser Met Ser Asp Ile Arg Lys Asp Leu Glu Glu Arg Phe Asp Lys
1               5                   10                  15
```

```
Leu Val Glu Ala Leu Lys Asn Lys Val Asp Lys Met Lys Ala Ala Phe
             20                  25                  30

Arg Lys Asp Gln Phe His Glu Glu Arg Met Lys Asp Trp Phe Lys Asp
         35                  40                  45

Leu Arg Lys Glu Val Glu Gln Met Arg Arg Ala Val Arg Asn Tyr Ala
     50                  55                  60

Ser Glu Ala Leu Ser Lys Ile Asn Asp Leu Pro Ile Thr Ile Asp Asp
 65                  70                  75                  80

Lys Lys Leu Ala Ser Asn Asp Val Leu Lys Leu Val Ala Glu Val Trp
                 85                  90                  95

Lys Lys Leu Glu Ala Ile Leu Ala Asp Val Glu Ala Trp Phe Thr Gln
             100                 105                 110
```

<210> SEQ ID NO 18
<211> LENGTH: 115
<212> TYPE: PRT
<213> ORGANISM: Artificial Sequence
<220> FEATURE:
<223> OTHER INFORMATION: Synthetic

<400> SEQUENCE: 18

```
Gly Ser Leu Ser Asp Ile Arg Lys Asp Ala Glu Arg Phe Asp Lys
 1               5                  10                  15

Leu Val Glu Ala Val Lys Asn Lys Leu Asp Lys Met Lys Ala Ala Leu
             20                  25                  30

Arg Lys Glu Gly Gln Gln Glu Glu Arg Met Lys Asp Leu Met Lys Phe
         35                  40                  45

Met Arg Lys Glu Val Glu Gln Leu Arg Lys Ala Met Arg Asn Phe Leu
     50                  55                  60

Ser Glu Ala Leu Ser Lys Ile Asn Asp Met Pro Ile Thr Ile Asp Asp
 65                  70                  75                  80

Lys Lys Leu Ile Ser Asn Asp Leu Lys Lys Tyr Asp Ala Ile Ala Glu
                 85                  90                  95

Lys Lys Leu Glu Ala Met Lys Ala Asp Val Glu Arg Met Ala Thr Gln
             100                 105                 110

Gly Ser Trp
        115
```

<210> SEQ ID NO 19
<211> LENGTH: 82
<212> TYPE: PRT
<213> ORGANISM: Artificial Sequence
<220> FEATURE:
<223> OTHER INFORMATION: Synthetic

<400> SEQUENCE: 19

```
Gly Ser Met Ser Asp Ile Arg Lys Asp Leu Glu Glu Arg Phe Asp Lys
 1               5                  10                  15

Leu Val Glu Ala Leu Lys Lys Gly Gln Gly Arg Gln Lys Glu Val Glu
             20                  25                  30

Gln Met Arg Arg Ala Val Arg Asn Tyr Ala Ser Glu Ala Leu Ser Lys
         35                  40                  45

Ile Asn Asp Leu Pro Ile Thr Asn Asp Asp Lys Lys Leu Ala Ser Asn
     50                  55                  60

Asp Val Leu Lys Leu Val Ala Glu Val Trp Lys Lys Leu Glu Ala Ile
 65                  70                  75                  80

Leu Ala
```

```
<210> SEQ ID NO 20
<211> LENGTH: 85
<212> TYPE: PRT
<213> ORGANISM: Artificial Sequence
<220> FEATURE:
<223> OTHER INFORMATION: Synthetic

<400> SEQUENCE: 20

Gly Ser Leu Ser Asp Ile Arg Lys Asp Ala Glu Arg Phe Asp Lys
1               5                   10                  15

Leu Val Glu Ala Val Lys Asn Leu Gly Asn Gly Glu Lys Glu Val Glu
                20                  25                  30

Gln Leu Arg Lys Ala Met Arg Asn Phe Leu Ser Glu Ala Leu Ser Lys
            35                  40                  45

Ile Asn Asp Met Pro Ile Thr Asn Asp Lys Lys Leu Ile Ser Asn
        50                  55                  60

Asp Leu Lys Lys Tyr Asp Ala Ile Ala Glu Lys Lys Leu Glu Ala Met
65                  70                  75                  80

Lys Ala Gly Ser Trp
                85

<210> SEQ ID NO 21
<211> LENGTH: 90
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (50)..(50)
<223> OTHER INFORMATION: X is N or Y
<220> FEATURE:
<221> NAME/KEY: MISC_FEATURE
<222> LOCATION: (56)..(56)
<223> OTHER INFORMATION: X is N or I
<220> FEATURE:
<221> NAME/KEY: MISC_FEATURE
<222> LOCATION: (60)..(60)
<223> OTHER INFORMATION: X is K, E, T, M or Q
<220> FEATURE:
<221> NAME/KEY: MISC_FEATURE
<222> LOCATION: (83)..(90)
<223> OTHER INFORMATION: optionally absent

<400> SEQUENCE: 21

Gly Ser Met Ser Asp Ile Arg Lys Asp Leu Glu Glu Arg Phe Asp Lys
1               5                   10                  15

Leu Val Glu Ala Leu Lys Lys Gly Gln Gly Arg Gln Lys Glu Val Glu
                20                  25                  30

Gln Met Arg Arg Ala Val Arg Asn Tyr Ala Ser Glu Ala Leu Ser Lys
            35                  40                  45

Ile Xaa Asp Leu Pro Ile Thr Xaa Asp Lys Xaa Leu Ala Ser Asn
        50                  55                  60

Asp Val Leu Lys Leu Val Ala Glu Val Trp Lys Lys Leu Glu Ala Ile
65                  70                  75                  80

Leu Ala Asp Val Glu Ala Trp Phe Thr Gln
                85                  90

<210> SEQ ID NO 22
<211> LENGTH: 93
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (50)..(50)
<223> OTHER INFORMATION: X is N or Y
<220> FEATURE:
<221> NAME/KEY: MISC_FEATURE
<222> LOCATION: (56)..(56)
<223> OTHER INFORMATION: X is N or I
<220> FEATURE:
<221> NAME/KEY: MISC_FEATURE
<222> LOCATION: (60)..(60)
<223> OTHER INFORMATION: X is K, E, T, M, or Q
<220> FEATURE:
<221> NAME/KEY: MISC_FEATURE
<222> LOCATION: (83)..(90)
<223> OTHER INFORMATION: optionally absent

<400> SEQUENCE: 22

Gly Ser Leu Ser Asp Ile Arg Lys Asp Ala Glu Arg Arg Phe Asp Lys
1               5                   10                  15

Leu Val Glu Ala Val Lys Asn Leu Gly Asn Gly Glu Lys Glu Val Glu
                20                  25                  30

Gln Leu Arg Lys Ala Met Arg Asn Phe Leu Ser Glu Ala Leu Ser Lys
            35                  40                  45

Ile Xaa Asp Met Pro Ile Thr Xaa Asp Asp Lys Xaa Leu Ile Ser Asn
    50                  55                  60

Asp Leu Lys Lys Tyr Asp Ala Ile Ala Glu Lys Lys Leu Glu Ala Met
65                  70                  75                  80

Lys Ala Asp Val Glu Arg Met Ala Thr Gln Gly Ser Trp
                85                  90

<210> SEQ ID NO 23
<211> LENGTH: 65
<212> TYPE: PRT
<213> ORGANISM: Artificial Sequence
<220> FEATURE:
<223> OTHER INFORMATION: Synthetic

<400> SEQUENCE: 23

Gly Ser Cys Ser Asp Ile Arg Lys Asp Cys Glu Arg Arg Phe Asp Lys
1               5                   10                  15

Gly Asp Gly Gly Arg Lys Ala Met Arg Asn Phe Leu Ser Glu Cys Leu
                20                  25                  30

Ser Lys Ile Asn Asp Met Pro Ile Thr Asn Asp Asp Lys Lys Leu Cys
            35                  40                  45

Ser Asn Asp Leu Lys Lys Tyr Asp Ala Ile Ala Glu Lys Lys Gly Ser
    50                  55                  60

Trp
65

<210> SEQ ID NO 24
<211> LENGTH: 65
<212> TYPE: PRT
<213> ORGANISM: Artificial Sequence
<220> FEATURE:
<223> OTHER INFORMATION: Synthetic

<400> SEQUENCE: 24

Gly Ser Leu Ser Asp Cys Arg Lys Asp Cys Glu Arg Arg Phe Asp Lys
1               5                   10                  15

Gly Asp Gly Gly Arg Lys Ala Met Arg Asn Phe Leu Ser Glu Cys Leu
                20                  25                  30

Ser Cys Ile Asn Asp Met Pro Ile Thr Asn Asp Asp Lys Lys Leu Ile
```

```
                35                  40                  45
Ser Asn Asp Leu Lys Lys Tyr Asp Ala Ile Ala Glu Lys Lys Gly Ser
    50                  55                  60
Trp
65

<210> SEQ ID NO 25
<211> LENGTH: 62
<212> TYPE: PRT
<213> ORGANISM: Artificial Sequence
<220> FEATURE:
<223> OTHER INFORMATION: Synthetic

<400> SEQUENCE: 25

Gly Ser Cys Ser Asp Ile Arg Lys Asp Ala Glu Arg Arg Phe Asp Lys
1               5                   10                  15

Gly Asp Gly Gly Arg Lys Ala Trp Arg Asn Phe Leu Ser Glu Phe Leu
            20                  25                  30

Ser Lys Ile Asn Asp Met Pro Ile Thr Asn Asp Lys Lys Leu Cys
        35                  40                  45

Ser Asn Asp Leu Lys Lys Tyr Leu Ala Ile Ala Glu Lys Lys
    50                  55                  60

<210> SEQ ID NO 26
<211> LENGTH: 62
<212> TYPE: PRT
<213> ORGANISM: Artificial Sequence
<220> FEATURE:
<223> OTHER INFORMATION: Synthetic

<400> SEQUENCE: 26

Gly Ser Leu Ser Asp Cys Arg Lys Asp Ala Glu Arg Arg Phe Asp Lys
1               5                   10                  15

Gly Asp Gly Gly Arg Lys Ala Trp Arg Asn Phe Leu Ser Glu Phe Leu
            20                  25                  30

Ser Cys Ile Asn Asp Met Pro Ile Thr Asn Asp Asp Lys Lys Leu Ile
        35                  40                  45

Ser Asn Asp Leu Lys Lys Tyr Leu Ala Ile Ala Glu Lys Lys
    50                  55                  60

<210> SEQ ID NO 27
<211> LENGTH: 62
<212> TYPE: PRT
<213> ORGANISM: Artificial Sequence
<220> FEATURE:
<223> OTHER INFORMATION: Synthetic

<400> SEQUENCE: 27

Gly Ser Leu Ser Asp Ile Arg Lys Asp Cys Glu Arg Arg Phe Asp Lys
1               5                   10                  15

Gly Asp Gly Gly Arg Lys Ala Trp Arg Asn Phe Leu Ser Glu Cys Leu
            20                  25                  30

Ser Lys Ile Asn Asp Met Pro Ile Thr Asn Asp Lys Lys Leu Ile
        35                  40                  45

Ser Asn Asp Leu Lys Lys Tyr Leu Ala Ile Ala Glu Lys Lys
    50                  55                  60

<210> SEQ ID NO 28
<211> LENGTH: 62
<212> TYPE: PRT
<213> ORGANISM: Artificial Sequence
```

-continued

<220> FEATURE:
<223> OTHER INFORMATION: Synthetic

<400> SEQUENCE: 28

Gly Ser Leu Ser Asp Ile Cys Lys Asp Ala Glu Arg Arg Phe Asp Lys
1               5                   10                  15

Gly Asp Gly Gly Arg Lys Ala Trp Arg Asn Phe Leu Ser Glu Phe Leu
            20                  25                  30

Ser Lys Ile Asn Asp Met Pro Ile Thr Asn Asp Lys Lys Leu Ile
        35                  40                  45

Ser Asn Asp Cys Lys Lys Tyr Leu Ala Ile Ala Glu Lys Lys
    50                  55                  60

<210> SEQ ID NO 29
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optinally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is R, A, I, M or V
<220> FEATURE:
<221> NAME/KEY: MISC_FEATURE
<222> LOCATION: (10)..(10)
<223> OTHER INFORMATION: X is L, A or V
<220> FEATURE:
<221> NAME/KEY: MISC_FEATURE
<222> LOCATION: (12)..(12)
<223> OTHER INFORMATION: X is E, R, K, or D
<220> FEATURE:
<221> NAME/KEY: MISC_FEATURE
<222> LOCATION: (14)..(14)
<223> OTHER INFORMATION: X is L, F, I or A
<220> FEATURE:
<221> NAME/KEY: MISC_FEATURE
<222> LOCATION: (17)..(17)
<223> OTHER INFORMATION: X is L, F, or A
<220> FEATURE:
<221> NAME/KEY: MISC_FEATURE
<222> LOCATION: (18)..(18)
<223> OTHER INFORMATION: X is L, V, or F
<220> FEATURE:
<221> NAME/KEY: MISC_FEATURE
<222> LOCATION: (21)..(21)
<223> OTHER INFORMATION: X is E, V, F, or L
<220> FEATURE:
<221> NAME/KEY: MISC_FEATURE
<222> LOCATION: (25)..(25)
<223> OTHER INFORMATION: X is M, L, F, or V
<220> FEATURE:
<221> NAME/KEY: MISC_FEATURE
<222> LOCATION: (28)..(28)
<223> OTHER INFORMATION: X is M, E, F, or I
<220> FEATURE:
<221> NAME/KEY: MISC_FEATURE
<222> LOCATION: (32)..(32)
<223> OTHER INFORMATION: X is M, L, F, or I
<220> FEATURE:
<221> NAME/KEY: MISC_FEATURE
<222> LOCATION: (35)..(35)
<223> OTHER INFORMATION: X is R, E ,G or D
<220> FEATURE:
<221> NAME/KEY: MISC_FEATURE
<222> LOCATION: (36)..(36)

-continued

```
<223> OTHER INFORMATION: X is G, D, P, W or Q
<220> FEATURE:
<221> NAME/KEY: MISC_FEATURE
<222> LOCATION: (37)..(37)
<223> OTHER INFORMATION: X is Q, I, P or F
<220> FEATURE:
<221> NAME/KEY: MISC_FEATURE
<222> LOCATION: (38)..(38)
<223> OTHER INFORMATION: X is R, Q, K, S or H
<220> FEATURE:
<221> NAME/KEY: MISC_FEATURE
<222> LOCATION: (42)..(42)
<223> OTHER INFORMATION: X is M, K, R or A
<220> FEATURE:
<221> NAME/KEY: MISC_FEATURE
<222> LOCATION: (45)..(45)
<223> OTHER INFORMATION: X is W, L, M or K
<220> FEATURE:
<221> NAME/KEY: MISC_FEATURE
<222> LOCATION: (46)..(46)
<223> OTHER INFORMATION: X is A, F, M or K
<220> FEATURE:
<221> NAME/KEY: MISC_FEATURE
<222> LOCATION: (48)..(48)
<223> OTHER INFORMATION: X is I, F, L, E, D or K
<220> FEATURE:
<221> NAME/KEY: MISC_FEATURE
<222> LOCATION: (49)..(49)
<223> OTHER INFORMATION: X is A, V, M, F, or L
<220> FEATURE:
<221> NAME/KEY: MISC_FEATURE
<222> LOCATION: (51)..(51)
<223> OTHER INFORMATION: X is D, K, Y, or E
<220> FEATURE:
<221> NAME/KEY: MISC_FEATURE
<222> LOCATION: (53)..(53)
<223> OTHER INFORMATION: X is F, V, A, R or M
<220> FEATURE:
<221> NAME/KEY: MISC_FEATURE
<222> LOCATION: (56)..(56)
<223> OTHER INFORMATION: X is F, V, A, L or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, V, I or Y
<220> FEATURE:
<221> NAME/KEY: MISC_FEATURE
<222> LOCATION: (64)..(64)
<223> OTHER INFORMATION: X is L, E or A
<220> FEATURE:
<221> NAME/KEY: MISC_FEATURE
<222> LOCATION: (67)..(67)
<223> OTHER INFORMATION: X is L or A
<220> FEATURE:
<221> NAME/KEY: MISC_FEATURE
<222> LOCATION: (72)..(72)
<223> OTHER INFORMATION: X is N or Y
<220> FEATURE:
<221> NAME/KEY: MISC_FEATURE
<222> LOCATION: (74)..(74)
<223> OTHER INFORMATION: X is M, L or Y
<220> FEATURE:
<221> NAME/KEY: MISC_FEATURE
<222> LOCATION: (78)..(78)
<223> OTHER INFORMATION: X is N or I
<220> FEATURE:
<221> NAME/KEY: MISC_FEATURE
<222> LOCATION: (80)..(80)
<223> OTHER INFORMATION: X is D, Q or K
<220> FEATURE:
<221> NAME/KEY: MISC_FEATURE
```

```
<222> LOCATION: (82)..(82)
<223> OTHER INFORMATION: X is K, E, T, M or Q
<220> FEATURE:
<221> NAME/KEY: MISC_FEATURE
<222> LOCATION: (84)..(84)
<223> OTHER INFORMATION: X is I, T, M, V or A
<220> FEATURE:
<221> NAME/KEY: MISC_FEATURE
<222> LOCATION: (88)..(88)
<223> OTHER INFORMATION: X is L, T, V or I
<220> FEATURE:
<221> NAME/KEY: MISC_FEATURE
<222> LOCATION: (89)..(89)
<223> OTHER INFORMATION: X is L, K or I
<220> FEATURE:
<221> NAME/KEY: MISC_FEATURE
<222> LOCATION: (91)..(91)
<223> OTHER INFORMATION: X is F, Y, K, E or L
<220> FEATURE:
<221> NAME/KEY: MISC_FEATURE
<222> LOCATION: (92)..(92)
<223> OTHER INFORMATION: X is D, A, V or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A, M or L
<220> FEATURE:
<221> NAME/KEY: MISC_FEATURE
<222> LOCATION: (96)..(96)
<223> OTHER INFORMATION: X is E, K, F or W
<220> FEATURE:
<221> NAME/KEY: MISC_FEATURE
<222> LOCATION: (99)..(99)
<223> OTHER INFORMATION: X is L, I or V
<220> FEATURE:
<221> NAME/KEY: MISC_FEATURE
<222> LOCATION: (101)..(101)
<223> OTHER INFORMATION: X is L or A
<220> FEATURE:
<221> NAME/KEY: MISC_FEATURE
<222> LOCATION: (102)..(102)
<223> OTHER INFORMATION: X is F, M, L, E or I
<220> FEATURE:
<221> NAME/KEY: MISC_FEATURE
<222> LOCATION: (103)..(103)
<223> OTHER INFORMATION: X is L, K, V, M or A
<220> FEATURE:
<221> NAME/KEY: MISC_FEATURE
<222> LOCATION: (106)..(106)
<223> OTHER INFORMATION: X is A, V, or I
<220> FEATURE:
<221> NAME/KEY: MISC_FEATURE
<222> LOCATION: (108)..(108)
<223> OTHER INFORMATION: X is E, R, D, K, I or A
<220> FEATURE:
<221> NAME/KEY: MISC_FEATURE
<222> LOCATION: (109)..(109)
<223> OTHER INFORMATION: X is A, M, K, L or W
<220> FEATURE:
<221> NAME/KEY: MISC_FEATURE
<222> LOCATION: (110)..(110)
<223> OTHER INFORMATION: X is A, F or V
<220> FEATURE:
<221> NAME/KEY: MISC_FEATURE
<222> LOCATION: (113)..(115)
<223> OTHER INFORMATION: optionally absent

<400> SEQUENCE: 29

Gly Ser Xaa Ser Asp Xaa Arg Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30
```

```
Arg Lys Xaa Xaa Xaa Glu Glu Arg Xaa Lys Asp Xaa Xaa Lys Xaa
            35                  40                  45

Xaa Arg Xaa Glu Xaa Glu Gln Xaa Arg Xaa Ala Xaa Arg Asn Xaa Xaa
 50                  55                  60

Ser Glu Xaa Leu Ser Lys Ile Xaa Asp Xaa Pro Ile Thr Xaa Asp Xaa
 65                  70                  75                  80

Lys Xaa Leu Xaa Ser Asn Asp Xaa Xaa Lys Xaa Xaa Ala Xaa Xaa Xaa
                 85                  90                  95

Lys Lys Xaa Glu Xaa Xaa Xaa Ala Asp Xaa Glu Xaa Xaa Xaa Thr Gln
            100                 105                 110

Gly Ser Trp
        115

<210> SEQ ID NO 30
<211> LENGTH: 115
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(2)
<223> OTHER INFORMATION: optinally absent
<220> FEATURE:
<221> NAME/KEY: MISC_FEATURE
<222> LOCATION: (3)..(3)
<223> OTHER INFORMATION: X is M, L, R or F
<220> FEATURE:
<221> NAME/KEY: MISC_FEATURE
<222> LOCATION: (6)..(6)
<223> OTHER INFORMATION: X is I or M
<220> FEATURE:
<221> NAME/KEY: MISC_FEATURE
<222> LOCATION: (10)..(10)
<223> OTHER INFORMATION: X is L or A
<220> FEATURE:
<221> NAME/KEY: MISC_FEATURE
<222> LOCATION: (12)..(12)
<223> OTHER INFORMATION: X is E, R, or D
<220> FEATURE:
<221> NAME/KEY: MISC_FEATURE
<222> LOCATION: (14)..(14)
<223> OTHER INFORMATION: X is F or A
<220> FEATURE:
<221> NAME/KEY: MISC_FEATURE
<222> LOCATION: (17)..(17)
<223> OTHER INFORMATION: X is L, F or A
<220> FEATURE:
<221> NAME/KEY: MISC_FEATURE
<222> LOCATION: (18)..(18)
<223> OTHER INFORMATION: X is V or F
<220> FEATURE:
<221> NAME/KEY: MISC_FEATURE
<222> LOCATION: (21)..(21)
<223> OTHER INFORMATION: X is A, V or L
<220> FEATURE:
<221> NAME/KEY: MISC_FEATURE
<222> LOCATION: (25)..(25)
<223> OTHER INFORMATION: X is F, W or L
<220> FEATURE:
<221> NAME/KEY: MISC_FEATURE
<222> LOCATION: (28)..(28)
<223> OTHER INFORMATION: X is F, M or I
<220> FEATURE:
<221> NAME/KEY: MISC_FEATURE
<222> LOCATION: (32)..(32)
<223> OTHER INFORMATION: X is F, L or I
<220> FEATURE:
<221> NAME/KEY: MISC_FEATURE
<222> LOCATION: (35)..(35)
<223> OTHER INFORMATION: X is E, G or D
<220> FEATURE:
<221> NAME/KEY: MISC_FEATURE
```

```
<222> LOCATION: (36)..(36)
<223> OTHER INFORMATION: X is E, G, Q, or W
<220> FEATURE:
<221> NAME/KEY: MISC_FEATURE
<222> LOCATION: (37)..(37)
<223> OTHER INFORMATION: X is I, P, Q, or F
<220> FEATURE:
<221> NAME/KEY: MISC_FEATURE
<222> LOCATION: (38)..(38)
<223> OTHER INFORMATION: X is K, S, Q, or H
<220> FEATURE:
<221> NAME/KEY: MISC_FEATURE
<222> LOCATION: (42)..(42)
<223> OTHER INFORMATION: X is M, R, or A
<220> FEATURE:
<221> NAME/KEY: MISC_FEATURE
<222> LOCATION: (45)..(45)
<223> OTHER INFORMATION: X is W, L, or M
<220> FEATURE:
<221> NAME/KEY: MISC_FEATURE
<222> LOCATION: (46)..(46)
<223> OTHER INFORMATION: X is K, F, or M
<220> FEATURE:
<221> NAME/KEY: MISC_FEATURE
<222> LOCATION: (48)..(48)
<223> OTHER INFORMATION: X is L, F, K or D
<220> FEATURE:
<221> NAME/KEY: MISC_FEATURE
<222> LOCATION: (49)..(49)
<223> OTHER INFORMATION: X is A, M or L
<220> FEATURE:
<221> NAME/KEY: MISC_FEATURE
<222> LOCATION: (51)..(51)
<223> OTHER INFORMATION: X is Y or K
<220> FEATURE:
<221> NAME/KEY: MISC_FEATURE
<222> LOCATION: (53)..(53)
<223> OTHER INFORMATION: X is V, A or M
<220> FEATURE:
<221> NAME/KEY: MISC_FEATURE
<222> LOCATION: (56)..(56)
<223> OTHER INFORMATION: X is L, A or M
<220> FEATURE:
<221> NAME/KEY: MISC_FEATURE
<222> LOCATION: (58)..(58)
<223> OTHER INFORMATION: X is K or R
<220> FEATURE:
<221> NAME/KEY: MISC_FEATURE
<222> LOCATION: (60)..(60)
<223> OTHER INFORMATION: X is V, M or I
<220> FEATURE:
<221> NAME/KEY: MISC_FEATURE
<222> LOCATION: (63)..(63)
<223> OTHER INFORMATION: X is F, R, I or Y
<220> FEATURE:
<221> NAME/KEY: MISC_FEATURE
<222> LOCATION: (64)..(64)
<223> OTHER INFORMATION: X is L, E or A
<220> FEATURE:
<221> NAME/KEY: MISC_FEATURE
<222> LOCATION: (67)..(67)
<223> OTHER INFORMATION: X is L or A
<220> FEATURE:
<221> NAME/KEY: MISC_FEATURE
<222> LOCATION: (74)..(74)
<223> OTHER INFORMATION: X is L or M
<220> FEATURE:
<221> NAME/KEY: MISC_FEATURE
<222> LOCATION: (80)..(80)
<223> OTHER INFORMATION: X is D or Q
<220> FEATURE:
<221> NAME/KEY: MISC_FEATURE
<222> LOCATION: (84)..(84)
<223> OTHER INFORMATION: X is I, M or A
<220> FEATURE:
<221> NAME/KEY: MISC_FEATURE
<222> LOCATION: (88)..(88)
<223> OTHER INFORMATION: X is I, L or V
<220> FEATURE:
```

-continued

```
<221> NAME/KEY: MISC_FEATURE
<222> LOCATION: (89)..(89)
<223> OTHER INFORMATION: X is I, L or K
<220> FEATURE:
<221> NAME/KEY: MISC_FEATURE
<222> LOCATION: (91)..(91)
<223> OTHER INFORMATION: X is F, Y, E, or L
<220> FEATURE:
<221> NAME/KEY: MISC_FEATURE
<222> LOCATION: (92)..(92)
<223> OTHER INFORMATION: X is D, A, V, or M
<220> FEATURE:
<221> NAME/KEY: MISC_FEATURE
<222> LOCATION: (94)..(94)
<223> OTHER INFORMATION: X is E, I or R
<220> FEATURE:
<221> NAME/KEY: MISC_FEATURE
<222> LOCATION: (95)..(95)
<223> OTHER INFORMATION: X is V, A or L
<220> FEATURE:
<221> NAME/KEY: MISC_FEATURE
<222> LOCATION: (96)..(96)
<223> OTHER INFORMATION: X is E, F or W
<220> FEATURE:
<221> NAME/KEY: MISC_FEATURE
<222> LOCATION: (99)..(99)
<223> OTHER INFORMATION: X is L or I
<220> FEATURE:
<221> NAME/KEY: MISC_FEATURE
<222> LOCATION: (102)..(102)
<223> OTHER INFORMATION: X is M, L or I
<220> FEATURE:
<221> NAME/KEY: MISC_FEATURE
<222> LOCATION: (103)..(103)
<223> OTHER INFORMATION: X is K, A, M or L
<220> FEATURE:
<221> NAME/KEY: MISC_FEATURE
<222> LOCATION: (106)..(106)
<223> OTHER INFORMATION: X is A, V or I
<220> FEATURE:
<221> NAME/KEY: MISC_FEATURE
<222> LOCATION: (108)..(108)
<223> OTHER INFORMATION: X is R, D, I or A
<220> FEATURE:
<221> NAME/KEY: MISC_FEATURE
<222> LOCATION: (109)..(109)
<223> OTHER INFORMATION: X is M, K, L or W
<220> FEATURE:
<221> NAME/KEY: MISC_FEATURE
<222> LOCATION: (110)..(110)
<223> OTHER INFORMATION: X is A, F, or V
<220> FEATURE:
<221> NAME/KEY: MISC_FEATURE
<222> LOCATION: (113)..(115)
<223> OTHER INFORMATION: optionally absent

<400> SEQUENCE: 30

Gly Ser Xaa Ser Asp Xaa Arg Lys Asp Xaa Glu Xaa Arg Xaa Asp Lys
1               5                   10                  15

Xaa Xaa Glu Ala Xaa Lys Asn Lys Xaa Asp Lys Xaa Lys Ala Ala Xaa
            20                  25                  30

Arg Lys Xaa Xaa Xaa Xaa Glu Glu Arg Xaa Lys Asp Xaa Xaa Lys Xaa
        35                  40                  45

Xaa Arg Xaa Glu Xaa Glu Gln Xaa Arg Xaa Ala Xaa Arg Asn Xaa Xaa
    50                  55                  60

Ser Glu Xaa Leu Ser Lys Ile Asn Asp Xaa Pro Ile Thr Asn Asp Xaa
65                  70                  75                  80

Lys Lys Leu Xaa Ser Asn Asp Xaa Xaa Lys Xaa Xaa Ala Xaa Xaa Xaa
                85                  90                  95

Lys Lys Xaa Glu Ala Xaa Xaa Ala Asp Xaa Glu Xaa Xaa Xaa Thr Gln
            100                 105                 110
```

```
Gly Ser Trp
        115

<210> SEQ ID NO 31
<211> LENGTH: 116
<212> TYPE: PRT
<213> ORGANISM: Artificial Sequence
<220> FEATURE:
<223> OTHER INFORMATION: Synthetic

<400> SEQUENCE: 31

Gly Ser Ile Ser Asp Ile Arg Lys Asp Ala Glu Val Arg Met Asp Lys
1               5                   10                  15

Ala Val Glu Ala Phe Lys Asn Lys Leu Asp Lys Phe Lys Ala Ala Val
            20                  25                  30

Arg Lys Val Phe Pro Thr Glu Glu Arg Ile Lys Asp Trp Leu Lys Ile
        35                  40                  45

Val Arg Gly Glu Ala Trp Gln Ala Arg Val Ala Val Arg Asn Val Gly
    50                  55                  60

Arg Asp Ala Asn Asp Lys Ala Ala Leu Gly Lys Asp Lys Glu Ile
65                  70                  75                  80

Asn Trp Phe Asp Ile Ser Gln Ser Leu Trp Asp Val Gln Lys Leu Thr
                85                  90                  95

Asp Ala Ala Ile Lys Lys Ile Glu Ala Ala Leu Ala Asp Met Glu Ala
            100                 105                 110

Trp Leu Thr Gln
        115

<210> SEQ ID NO 32
<211> LENGTH: 8
<212> TYPE: PRT
<213> ORGANISM: Artificial Sequence
<220> FEATURE:
<223> OTHER INFORMATION: Synthetic

<400> SEQUENCE: 32

Leu Glu His His His His His His
1               5

<210> SEQ ID NO 33
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is M, L or C
<220> FEATURE:
<221> NAME/KEY: MISC_FEATURE
<222> LOCATION: (6)..(6)
<223> OTHER INFORMATION: X is I or C
<220> FEATURE:
<221> NAME/KEY: MISC_FEATURE
<222> LOCATION: (7)..(7)
<223> OTHER INFORMATION: X is R or C
<220> FEATURE:
<221> NAME/KEY: MISC_FEATURE
<222> LOCATION: (10)..(10)
<223> OTHER INFORMATION: X is L, A, or C
<220> FEATURE:
<221> NAME/KEY: MISC_FEATURE
<222> LOCATION: (12)..(12)
<223> OTHER INFORMATION: X is E, R, or absent
<220> FEATURE:
<221> NAME/KEY: MISC_FEATURE
```

<222> LOCATION: (16)..(16)
<223> OTHER INFORMATION: X is L or G

<400> SEQUENCE: 33

Gly Ser Xaa Ser Asp Xaa Xaa Lys Asp Xaa Glu Xaa Phe Asp Lys Xaa
1               5                   10                  15

<210> SEQ ID NO 34
<211> LENGTH: 76
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: X is L or V
<220> FEATURE:
<221> NAME/KEY: MISC_FEATURE
<222> LOCATION: (6)..(6)
<223> OTHER INFORMATION: X is K or N
<220> FEATURE:
<221> NAME/KEY: MISC_FEATURE
<222> LOCATION: (7)..(7)
<223> OTHER INFORMATION: X is L or G
<220> FEATURE:
<221> NAME/KEY: MISC_FEATURE
<222> LOCATION: (8)..(8)
<223> OTHER INFORMATION: X is Q or G
<220> FEATURE:
<221> NAME/KEY: MISC_FEATURE
<222> LOCATION: (9)..(9)
<223> OTHER INFORMATION: X is N or G
<220> FEATURE:
<221> NAME/KEY: MISC_FEATURE
<222> LOCATION: (10)..(10)
<223> OTHER INFORMATION: X is R or G
<220> FEATURE:
<221> NAME/KEY: MISC_FEATURE
<222> LOCATION: (11)..(11)
<223> OTHER INFORMATION: X is Q or E
<220> FEATURE:
<221> NAME/KEY: MISC_FEATURE
<222> LOCATION: (17)..(17)
<223> OTHER INFORMATION: X is L or M
<220> FEATURE:
<221> NAME/KEY: MISC_FEATURE
<222> LOCATION: (19)..(19)
<223> OTHER INFORMATION: X is R or K
<220> FEATURE:
<221> NAME/KEY: MISC_FEATURE
<222> LOCATION: (21)..(21)
<223> OTHER INFORMATION: X is V or M
<220> FEATURE:
<221> NAME/KEY: MISC_FEATURE
<222> LOCATION: (24)..(24)
<223> OTHER INFORMATION: X is Y or F
<220> FEATURE:
<221> NAME/KEY: MISC_FEATURE
<222> LOCATION: (25)..(25)
<223> OTHER INFORMATION: X is A or L
<220> FEATURE:
<221> NAME/KEY: MISC_FEATURE
<222> LOCATION: (33)..(33)
<223> OTHER INFORMATION: X is N or Y
<220> FEATURE:
<221> NAME/KEY: MISC_FEATURE
<222> LOCATION: (35)..(35)
<223> OTHER INFORMATION: X is L or M
<220> FEATURE:
<221> NAME/KEY: MISC_FEATURE
<222> LOCATION: (39)..(39)
<223> OTHER INFORMATION: X is N or I
<220> FEATURE:
<221> NAME/KEY: MISC_FEATURE
<222> LOCATION: (43)..(43)
<223> OTHER INFORMATION: X is K, E, T, M, or Q

```
<220> FEATURE:
<221> NAME/KEY: MISC_FEATURE
<222> LOCATION: (45)..(45)
<223> OTHER INFORMATION: X is A or I
<220> FEATURE:
<221> NAME/KEY: MISC_FEATURE
<222> LOCATION: (49)..(49)
<223> OTHER INFORMATION: X is V or L
<220> FEATURE:
<221> NAME/KEY: MISC_FEATURE
<222> LOCATION: (50)..(50)
<223> OTHER INFORMATION: X is K or L
<220> FEATURE:
<221> NAME/KEY: MISC_FEATURE
<222> LOCATION: (52)..(52)
<223> OTHER INFORMATION: X is Y or L
<220> FEATURE:
<221> NAME/KEY: MISC_FEATURE
<222> LOCATION: (53)..(53)
<223> OTHER INFORMATION: X is V or D
<220> FEATURE:
<221> NAME/KEY: MISC_FEATURE
<222> LOCATION: (55)..(55)
<223> OTHER INFORMATION: X is E or I
<220> FEATURE:
<221> NAME/KEY: MISC_FEATURE
<222> LOCATION: (56)..(56)
<223> OTHER INFORMATION: X is V or A
<220> FEATURE:
<221> NAME/KEY: MISC_FEATURE
<222> LOCATION: (57)..(57)
<223> OTHER INFORMATION: X is W or E
<220> FEATURE:
<221> NAME/KEY: MISC_FEATURE
<222> LOCATION: (63)..(63)
<223> OTHER INFORMATION: X is I or M
<220> FEATURE:
<221> NAME/KEY: MISC_FEATURE
<222> LOCATION: (64)..(64)
<223> OTHER INFORMATION: X is L or K
<220> FEATURE:
<221> NAME/KEY: MISC_FEATURE
<222> LOCATION: (66)..(76)
<223> OTHER INFORMATION: optinally absent
<220> FEATURE:
<221> NAME/KEY: MISC_FEATURE
<222> LOCATION: (66)..(66)
<223> OTHER INFORMATION: X is G or D
<220> FEATURE:
<221> NAME/KEY: MISC_FEATURE
<222> LOCATION: (67)..(67)
<223> OTHER INFORMATION: X is S or V
<220> FEATURE:
<221> NAME/KEY: MISC_FEATURE
<222> LOCATION: (68)..(68)
<223> OTHER INFORMATION: X is W or E
<220> FEATURE:
<221> NAME/KEY: MISC_FEATURE
<222> LOCATION: (69)..(69)
<223> OTHER INFORMATION: X is R or A
<220> FEATURE:
<221> NAME/KEY: MISC_FEATURE
<222> LOCATION: (70)..(70)
<223> OTHER INFORMATION: X is W or M
<220> FEATURE:
<221> NAME/KEY: MISC_FEATURE
<222> LOCATION: (71)..(71)
<223> OTHER INFORMATION: X is F or A

<400> SEQUENCE: 34

Val Glu Ala Xaa Lys Xaa Xaa Xaa Xaa Xaa Xaa Lys Glu Val Glu Gln
1               5                   10                  15

Xaa Arg Xaa Ala Xaa Arg Asn Xaa Xaa Ser Glu Ala Leu Ser Lys Ile
            20                  25                  30

Xaa Asp Xaa Pro Ile Thr Xaa Asp Asp Lys Xaa Leu Xaa Ser Asn Asp
        35                  40                  45
```

```
Xaa Xaa Lys Xaa Xaa Ala Xaa Xaa Lys Lys Leu Glu Ala Xaa Xaa
    50              55                  60

Ala Xaa Xaa Xaa Xaa Xaa Xaa Thr Gln Gly Ser Trp
65              70                  75

<210> SEQ ID NO 35
<211> LENGTH: 65
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is C or L
<220> FEATURE:
<221> NAME/KEY: MISC_FEATURE
<222> LOCATION: (6)..(6)
<223> OTHER INFORMATION: X is I or C
<220> FEATURE:
<221> NAME/KEY: MISC_FEATURE
<222> LOCATION: (7)..(7)
<223> OTHER INFORMATION: X is R or C
<220> FEATURE:
<221> NAME/KEY: MISC_FEATURE
<222> LOCATION: (10)..(10)
<223> OTHER INFORMATION: X is A or C
<220> FEATURE:
<221> NAME/KEY: MISC_FEATURE
<222> LOCATION: (24)..(24)
<223> OTHER INFORMATION: X is M or W
<220> FEATURE:
<221> NAME/KEY: MISC_FEATURE
<222> LOCATION: (31)..(31)
<223> OTHER INFORMATION: X is C or F
<220> FEATURE:
<221> NAME/KEY: MISC_FEATURE
<222> LOCATION: (34)..(34)
<223> OTHER INFORMATION: X is C or K
<220> FEATURE:
<221> NAME/KEY: MISC_FEATURE
<222> LOCATION: (48)..(48)
<223> OTHER INFORMATION: X is C or I
<220> FEATURE:
<221> NAME/KEY: MISC_FEATURE
<222> LOCATION: (52)..(52)
<223> OTHER INFORMATION: X is C or L
<220> FEATURE:
<221> NAME/KEY: MISC_FEATURE
<222> LOCATION: (56)..(56)
<223> OTHER INFORMATION: X is D or L
<220> FEATURE:
<221> NAME/KEY: MISC_FEATURE
<222> LOCATION: (63)..(65)
<223> OTHER INFORMATION: optionally absent

<400> SEQUENCE: 35

Gly Ser Xaa Ser Asp Xaa Xaa Lys Asp Xaa Glu Arg Arg Phe Asp Lys
1               5                   10                  15

Gly Asp Gly Gly Arg Lys Ala Xaa Arg Asn Phe Leu Ser Glu Xaa Leu
            20                  25                  30

Ser Xaa Ile Asn Asp Met Pro Ile Thr Asn Asp Lys Lys Leu Xaa
        35                  40                  45

Ser Asn Asp Xaa Lys Lys Tyr Xaa Ala Ile Ala Glu Lys Lys Gly Ser
    50                  55                  60

Trp
65

<210> SEQ ID NO 36
<211> LENGTH: 16
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is M, L or C
<220> FEATURE:
<221> NAME/KEY: MISC_FEATURE
<222> LOCATION: (10)..(10)
<223> OTHER INFORMATION: X is L or A
<220> FEATURE:
<221> NAME/KEY: MISC_FEATURE
<222> LOCATION: (12)..(12)
<223> OTHER INFORMATION: X is E, R, or absent

<400> SEQUENCE: 36

Gly Ser Xaa Ser Asp Ile Arg Lys Asp Xaa Glu Xaa Phe Asp Lys Leu
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: X is L or C
<220> FEATURE:
<221> NAME/KEY: MISC_FEATURE
<222> LOCATION: (6)..(6)
<223> OTHER INFORMATION: X is I or C
<220> FEATURE:
<221> NAME/KEY: MISC_FEATURE
<222> LOCATION: (7)..(7)
<223> OTHER INFORMATION: X is R or C
<220> FEATURE:
<221> NAME/KEY: MISC_FEATURE
<222> LOCATION: (10)..(10)
<223> OTHER INFORMATION: X is A or C

<400> SEQUENCE: 37

Gly Ser Xaa Ser Asp Xaa Xaa Lys Asp Xaa Glu Arg Arg Phe Asp Lys
1               5                   10                  15

Gly
```

EPITOPE-SCAFFOLD IMMUNOGENS AGAINST RESPIRATORY SYNCYTIAL VIRUS (RSV)

CROSS REFERENCE

This application is a U.S. National Phase of International Application No. PCT/US2013/035408, filed Apr. 5, 2013, which claims priority to U.S. Provisional Application No. 61/620,797, filed Apr. 5, 2012; and U.S. Provisional Application No. 61/620,804, filed Apr. 5, 2012, the disclosures of which are hereby incorporated by reference in their entireties.

BACKGROUND

Respiratory Syncytial Virus (RSV) is the leading cause of viral death in infants worldwide and also causes disease in the elderly and immune-compromised. The current method for preventing RSV infection is passive immunization with Palivizumab (Pali), an FDA-licensed humanized monoclonal antibody that binds the F protein on the RSV surface. Though effective at preventing RSV infection, Pali treatment is not economically or logistically feasible on a global scale.

SUMMARY OF THE INVENTION

In a first aspect, the present invention provides isolated polypeptides comprising an amino acid sequence according to any of SEQ ID NOS:1-30, which can be used, for example, in the methods of the invention.

In another aspect, the present invention provides virus-like particles comprising the polypeptide of the invention.

In further aspects, the present invention provides isolated nucleic acids encoding the polypeptides of the invention; recombinant expression vectors comprising the isolated nucleic acids of the invention operatively linked to a promoter; and recombinant host cells comprising the recombinant expression vectors of the invention.

In a still further aspect, the present invention provides pharmaceutical compositions, comprising the polypeptide and/or virus-like particles of the invention, and a pharmaceutically acceptable carrier.

In another aspect, the present invention provides methods for treating a RSV infection, comprising administering to a subject infected with RSV an amount effective to treat the infection of the polypeptides, virus-like particles, or pharmaceutical compositions of the invention In a further aspect, the present invention provides methods for limiting development of an RSV infection, comprising administering to a subject at risk of RSV infection an amount effective to limit development of an RSV infection of the polypeptides, virus-like particles, or pharmaceutical compositions of the invention.

In a still further aspect, the present invention provides methods for generating an immune response in a subject, comprising administering to the subject an amount effective to generate an immune response of the polypeptides, virus-like particles, or pharmaceutical compositions of the invention.

In another aspect, the present invention provides pharmaceutical composition, comprising (a) isolated nucleic acids, recombinant expression vectors, and/or recombinant host cells of the invention; and (b) a pharmaceutically acceptable carrier.

In a further aspect, the present invention provides methods for monitoring an RSV-induced disease in a subject and/or monitoring response of the subject to immunization by an RSV vaccine, comprising contacting the polypeptides, the VLPs, or the pharmaceutical compositions of the invention with a bodily fluid from the subject and detecting RSV-binding antibodies in the bodily fluid of the subject.

In a still further aspect, the present invention provides methods for detecting RSV binding antibodies, comprising (a) contacting the polypeptides, the VLPs, or the compositions of the invention with a composition comprising a candidate RSV binding antibody under conditions suitable for binding of RSV antibodies to the polypeptide, VLP, or composition; and (b) detecting RSV antibody complexes with the polypeptide, VLP, or composition.

In another aspect, the present invention provides methods for producing RSV antibodies, comprising (a) administering to a subject an amount effective to generate an antibody response of the polypeptides, the VLPs, and/or the compositions of the invention; and (b) isolating antibodies produced by the subject.

BRIEF DESCRIPTION OF THE DRAWINGS

FIG. 3 is a sequence alignment of the different scaffolds and the sequence of the protein used as target topology (T93). The similarities in many of the positions were imposed by the surface that in the scaffolds was intentionally maintained the same as the target topology.

DETAILED DESCRIPTION OF THE INVENTION

Figure 1:
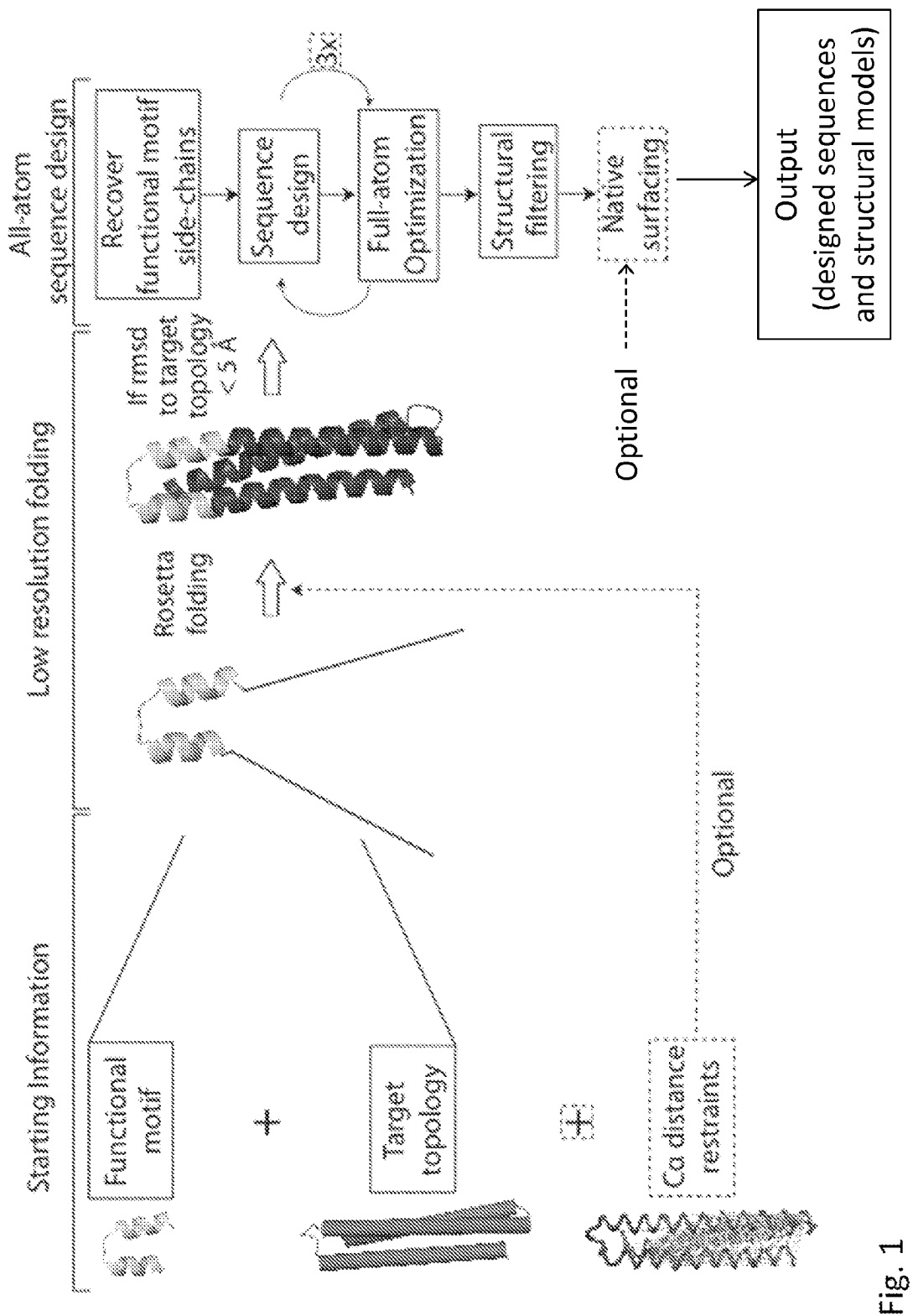
FIG. 1 is an overview of the computational procedure Fold From Loops. The procedure takes a functional site (such as the helical hairpin shown) that will be used as the folding nucleus and remain in fixed backbone conformation throughout the procedure. A target topology is supplied and distance constraints are (optionally) derived from the target topology structure to guide the folding trajectory. The polypeptide chain is extended from the folding nucleus and the chain is then folded. If the models produced are more than a cutoff root mean square deviation (rmsd) (e.g. 5 Å) away from the target topology, they are discarded. Otherwise, they enter cycles of design and full-atom optimization. The figure depicts 3 cycles of iterative design and optimization as a reasonable choice, but the number of cycles is to be chosen at the discretion of the user.

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, 2$^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, the singular forms "a", "an" and "the" include plural referents unless the context clearly dictates otherwise. "And" as used herein is interchangeably used with "or" unless expressly stated otherwise.

All embodiments of any aspect of the invention can be used in combination, unless the context clearly dictates otherwise.

In a first aspect, the present invention provides isolated polypeptides, comprising or consisting of an amino acid sequence according to the following:

(SEQ ID NO: 1)
(-/G)(-/S)(M/L/R/F)SD(R/A/I/M/V/L)(R/M)KD(L/A/V)E
(E/R/K/D)R(L/F/I/A)DK(L/F/A)(L/V/F/M)EA(A/V/F/I/L)
KNK(E/M/L/F/W/V)DK(F/M/E/I/V)KAA(M/L/F/I)RK(R/E/G/
D/Q)(G/D/P/W/E/Q)(Q/I/P/K/F)(R/Q/K/S/G/H)EER(M/K/
R/A)KD(W/L/M/K)(A/M/K/F)K(I/F/L/E/K/D)(A/V/M/F/L)R
(D/K/E/Y)E(F/V/A/R/M/L)EQ(F/L/A/V/M)R(K/R)A(V/M/I)
RN(F/R/V/I/A/Y)(L/E/A)(S)(E)(A/L)(L)(S)K(I)(N/Y)D (Y/M/L)(P)I(T)(N/I)(D)(D/Q/K)(K)(K/E/T/M/Q)(L)(T/
I/M/V/A)(S)(N)(D/K)(A/T/L/V/I)(K/L/I)K(F/Y/K/E/R/
L)(D/A/V/M)(A)(E/I/R)(V/A/M/L)(A/E/K/F/M/W)KK(L/I/
V)E(A/L)(F/M/L/E/I)(K/A/V/M/I/L)AD(A/V/I)E(E/R/D/
K/I/A)(A/M/K/L/W)(A/F/V/K)TQ(-/G)(-/S)(-/W).

The inventors have designed the polypeptides of the invention to elicit neutralizing antibodies with similar specificity as Palivizumab or Motavizumab. Palivizumab is a FDA-licensed therapeutic antibody that potently neutralizes Respiratory Syncytial Virus (RSV) by binding antigenic site A (also called "site II") on the RSV F surface glycoprotein. Motavizumab is an affinity-matured variant of Palivizumab. Thus, vaccine that elicits RSV-neutralizing antibodies similar to Palivizumab (Pali) or Motavizumab (Mota) is desired to protect against RSV infection. Pali and Mota bind to a conformational epitope on the RSV F protein. As disclosed herein, the inventors have developed a computational method to design de novo protein scaffolds for epitope conformational stabilization and presentation to the immune system. This method was applied to the Mota epitope to design the polypeptides of the invention, which are shown to be monomeric, highly thermostable, and extremely high binding affinities for Mota, indicating that the polypeptides have successfully stabilized the desired epitope conformation, as confirmed by crystal structure analysis. The inventors have also demonstrated that polypeptides falling within the scope of this genus can elicit neutralizing antibodies against RSV.

Parentheses represent variable positions in the polypeptide, with the recited amino acid residues as alternatives in these positions.

In one preferred embodiment, the polypeptides comprise or consist of an amino acid sequence according to the following:

(SEQ ID NO: 2)
(-/G)(-/S)(M/L/R/F)SD(R/A/I/M/V)RKD(L/A/V)E(E/R/K/
D)R(L/F/I/A)DK(L/F/A)(L/V/F)EA(A/V/F/L)KNK(M/L/F/
V)DK(F/M/E/I)KAA(M/L/F/I)RK(R/E/G/D)(G/D/P/W/Q)(Q/
I/P/F)(R/Q/K/S/H)EER(M/K/R/A)KD(W/L/M/K)(A/M/K/F)K
(I/F/L/E/K/D)(A/V/M/F/L)R(D/K/Y/E)E(F/V/A/R/M)EQ
(F/L/A/V/M)R(K/R)A(V/M/I)RN(F/R/V/I/Y)(L/E/A)SE(A/
L)LSKIND(Y/M/L)PITND(D/Q/K)KKL(T/I/M/V/A)SND(T/L/V/
I)(K/L/I)K(F/Y/K/E/L)(D/A/V/M)A(E/I/R)(V/A/M/L)
(E/K/F/W)KK(L/I/V)E(A/L)(F/M/L/E/I)(K/A/V/M/L)AD(A/
V/I)E(E/R/D/K/I/A)(A/M/K/L/W)(A/F/V)TQ(-/G)(-/S)
(-/W);
or (SEQ ID NO: 29)
(-/G)(-/S)(M/L/R/F)SD(R/A/I/M/V)RKD(L/A/V)E(E/R/K/
D)R(L/F/I/A)DK(L/F/A)(L/V/F)EA(A/V/F/L)KNK(M/L/F/
V)DK(F/M/E/I)KAA(M/L/F/I)RK(R/E/G/D)(G/D/P/W/Q)(Q/
I/P/F)(R/Q/K/S/H)EER(M/K/R/A)KD(W/L/M/K)(A/M/K/F)K
(I/F/L/E/K/D)(A/V/M/F/L)R(D/K/Y/E)E(F/V/A/R/M)EQ
(F/L/A/V/M)R(K/R)A(V/M/I)RN(F/R/V/I/Y)(L/E/A)SE(A/
L)LSKI(N/Y)D(Y/M/L)PIT(N/I)D(D/Q/K)K(K/E/T/M/Q)L(T/
I/M/V/A)SND(T/L/V/I)(K/L/I)K(F/Y/K/E/L)(D/A/V/M)A
(E/I/R)(V/A/M/L)(E/K/F/W)KK(L/I/V)E(A/L)(F/M/L/E/I)
(K/A/V/M/L)AD(A/V/I)E(E/R/D/K/I/A)(A/M/K/L/W)(A/F/
V)TQ(-/G)(-/S)(-/W)

Polypeptides according to this genus are those that are present in those polypeptides demonstrating the best range of activities, as demonstrated in the examples that follow.

In a further preferred embodiment, the polypeptides comprise or consist of an amino acid sequence according to the following:

(SEQ ID NO: 3)
(-/G)(-/S)(M/L/R/F)SD(I/M)RKD(L/A)E(E/R/D)R(F/A)DK
(L/F/A)(V/F)EA(A/V/L)KNK(L/F/W)DK(F/M/I)KAA(L/F/I)
RK(E/G/D)(G/D/W/Q)(Q/I/P/F)(Q/K/S/H)EER(M/R/A)KD
(W/L/M)(M/K/F)K(F/L/K/D)(A/M/L)R(Y/K)E(V/A/M)EQ(L/
A/M)R(K/R)A(V/M/I)RN(F/R/I/Y)(L/E/A)SE(A/L)LSKI(N/
Y)D(M/L)PIT(N/I)D(D/Q)K(K/E/T/M/Q)L(I/M/A)SND(L/V/
I)(K/L/I)K(F/Y/E/L)(D/A/V/M)A(E/I/R)(V/A/L)(E/F/W)
KK(L/I)EA(M/L/I)(K/A/M/L)AD(A/V/I)E(R/D/I/A)(M/K/
L/W)(A/F/V)TQ(-/G)(-/S)(-/W)
or

SEQ ID NO: 30
(-/G)(-/S)(M/L/R/F)SD(I/M)RKD(L/A)E(E/R/D)R(F/A)DK
(L/F/A)(V/F)EA(A/V/L)KNK(L/F/W)DK(F/M/I)KAA(L/F/I)
RK(E/G/D)(G/D/W/Q)(Q/I/P/F)(Q/K/S/H)EER(M/R/A)KD
(W/L/M)(M/K/F)K(F/L/K/D)(A/M/L)R(Y/K)E(V/A/M)EQ
(L/A/M)R(K/R)A(V/M/I)RN(F/R/I/Y)(L/E/A)SE(A/L)LSKI
ND(M/L)PITND(D/Q)KKL(I/M/A)SND(L/V/I)(K/L/I)K(F/Y/
E/L)(D/A/V/M)A(E/I/R)(V/A/L)(E/F/W)KK(L/I)EA(M/L/
I)(K/A/M/L)AD(A/V/I)E(R/D/I/A)(M/K/L/W)(A/F/V)TQ
(-/G)(-/S)(-/W).

Polypeptides according to this genus are those that have been exemplified by the inventors as eliciting neutralizing antibodies against RSV.

In a further preferred embodiment, the polypeptides comprise or consist of an amino acid sequence selected from the group consisting of

>FFL_001
(SEQ ID NO: 4)
GSRSDMRKDAERRFDKFVEAAKNKFDKFKAALRKGDIKEERRKDMKKLA

RKEAEQARRAVRNRLSELLSKINDMPITNDQKKLMSNDVLKFAAEEAEKK

IEALAADAEDKFTQGSW;

>FFL_002
(SEQ ID NO: 5)
GSLSDVRKDVEKRIDKALEAFKNKMDKEKAAFRKDPPSEERRKDKKKEF

REEREQVRKAIRNVLSEALSKINDLPITNDKKKLVSNDVIKKVAEMKKK

VELEVADVEKKVTQGSW;

>FFL_004
(SEQ ID NO: 6)
GSMSDARKDLEERLDKLLEAAKNKMDKFKAAMRKRGQREERRKKDWAKIV

RDEFEQFRKAVRNFLSEALSKINDYPITNDDKKLTSNDTKKFAAEVEKK

LEAFKADVEEAATQ;

>FFL_005
(SEQ ID NO: 7)
GSMSDIRKDLEERFDKLVEALKNKVDKMKAAFRKDQFHEERMKDWFKDL

RKEVEQMRRAVRNYASEALSKINDLPITNDDKKLASNDVLKLVAEVWKK

LEAILADVEAWFTQ;

>FFL_006
(SEQ ID NO: 8)
GSFSDIRKDAEDRADKAFEAAKNKFDKIKAAIRKDWPSEERAKDLMKKA

RYEMEQARRAIRNIESEALSKINDLPITNDQKKLASNDIIKEMARLFKK

LEALMADIEILVTQ;
and

>FFL_007
(SEQ ID NO: 9)
GSLSDIRKDAERRFDKLVEAVKNKLDKMKAALRKEGQQEERMKDLMKFM

RKEVEQLRKAMRNFLSEALSKINDMPITNDDKKLISNDLKKYDAIAEKK

LEAMKADVERMATQGSW.

Each of these polypeptides is demonstrated in the examples that follow to be monomeric, highly thermostable, and have extremely high binding affinities for Mota, indicating that the polypeptides have successfully stabilized the desired epitope conformation, and a number of these polypeptides have been shown to elicit neutralizing antibodies against RSV.

In another embodiment, the polypeptides comprise resistance mutants for Motavizumab and/or Palivizumab. These polypeptides can be used, for example, in a vaccine to protect against RSV strains that are resistant to Mota-like or Pali-like neutralizing antibodies, or to prevent the emergence of such resistant RSV strains, In such vaccines, it may be desirable to include epitope-scaffolds bearing resistance mutations within the RSV epitope. In this way, vaccination with "resistance mutant epitope-scaffolds" might induce antibodies that neutralize resistance mutant viruses and hence prevent the emergence of those resistance viruses. Similarly, the "resistance mutant epitope-scaffolds" could be used as reagents to isolate antibodies that neutralize resistance mutant viruses.

For Motavizumab, one established resistance mutation is K272E (Zhu et al. JID, 2011). For Palivizumab, several resistance mutations have been identified, including K272N, K272M, K272T, K272Q (Zhu et al. JID, 2011). Arbiza et al. J. Gen Virol 1992 identified resistance mutations K272E, K272T, N262Y and N268I and showed that these reduce binding by antibodies directed to this region on RSVF.

We have shown that the K272E and N262Y mutations introduced onto our epitope-scaffold RSV_1isea_FFL_001 significantly reduce binding by Mota or Pali. By structural similarity among the epitope-scaffolds, we expect that either of these mutations will have the same effect on binding to other scaffolds such as 005 and 007.

Exemplary such polypeptides include the following (note that the residue numbering for the mutations refers to the position in the RSV F protein sequence not in the epitope-scaffold itself).

RSV_1isea_FFL_001_resistance_mutants_at_pos272
(SEQ ID NO: 10)
GSRSDMRKDAERRFDKFVEAAKNKFDKFKAALRKGDIKEERRKDMKKLARKEA

EQARRAVRNRLSELLSKINDMPITNDQK[E, T, M, Q]LMSNDVLKFAAEAEKKIEAL

AADAEDKFTQGSW

RSV_1isea_FFL_005_resistance_mutants_at_pos272
(SEQ ID NO: 11)
GSMSDIRKDLEERFDKLVEALKNKVDKMKAAFRKDQFHEERMKDWFKDLRKEV

EQMRRAVRNYASEALSKINDLPITNDDK[E, T, M, Q]LASNDVLKLVAEVWKKLEAI

LADVEAWFTQ

```
RSV_1isea_FFL_007_resistance_mutants_at_pos272
                                                         (SEQ ID NO: 12)
GSLSDIRKDAERRFDKLVEAVKNKLDKMKAALRKEGQQEERMKDLMKFMRKEV

EQLRKAMRNFLSEALSKINDMPITNDDK[E, T, M, Q]LISNDLKKYDAIAEKKLEAM

KADVERMATQGSW

RSV_1isea_FFL_001_resistance_mutant_at_262
                                                         (SEQ ID NO: 13)
GSRSDMRKDAERRFDKFVEAAKNKFDKFKAALRKGDIKEERRKDMKKLARKEA

EQARRAVRNRLSELLSKIYDMPITNDQKKLMSNDVLKFAAEAEKKIEALAADAED

KFTQGSW

RSV_1isea_FFL_005_resistance_mutant_at_262
                                                         (SEQ ID NO: 14)
GSMSDIRKDLEERFDKLVEALKNKVDKMKAAFRKDQFHEERMKDWFKDLRKEV

EQMRRAVRNYASEALSKIYDLPITNDDKKLASNDVLKLVAEVWKKLEAILADVE

AWFTQ

RSV_1isea_FFL_007_resistance_mutant_at_262
                                                         (SEQ ID NO: 15)
GSLSDIRKDAERRFDKLVEAVKNKLDKMKAALRKEGQQEERMKDLMKFMRKEV

EQLRKAMRNFLSEALSKIYDMPITNDDKKLISNDLKKYDAIAEKKLEAMKADVER

MATQGSW

RSV_1isea_FFL_001_resistance_mutant_at_268
                                                         (SEQ ID NO: 16)
GSRSDMRKDAERRFDKFVEAAKNKFDKFKAALRKGDIKEERRKDMKKLARKEA

EQARRAVRNRLSELLSKINDMPITIDQKKLMSNDVLKFAAEAEKKIEALAADAED

KFTQGSW

RSV_1isea_FFL_005_resistance_mutant_at_268
                                                         (SEQ ID NO: 17)
GSMSDIRKDLEERFDKLVEALKNKVDKMKAAFRKDQFHEERMKDWFKDLRKEV

EQMRRAVRNYASEALSKINDLPITIDDKKLASNDVLKLVAEVWKKLEAILADVEA

WFTQ

RSV_1isea_FFL_007_resistance_mutant_at_268
                                                         (SEQ ID NO: 18)
GSLSDIRKDAERRFDKLVEAVKNKLDKMKAALRKEGQQEERMKDLMKFMRKEV

EQLRKAMRNFLSEALSKINDMPITIDDKKLISNDLKKYDAIAEKKLEAMKADVER

MATQGSW.
```

In another embodiment, the polypeptides comprise or consist of smaller epitope-scaffolds with similar properties to those disclosed above. Smaller scaffolds are potentially advantageous because they may contain fewer off-target epitopes, because they may be more amenable to particulate presentation by chemical conjugation, genetic fusion, or other means, and because smaller scaffolds may be more economical to produce commercially.

In one embodiment, the smaller scaffolds comprise or consist of an isolated peptide comprising an amino acid of the formula X1-X2, wherein X1 is

```
                                                         (SEQ ID NO: 33)
GS(M/L/C)SD(I/C)(R/C)KD(L/A/C)E(E/R/)FDK(L/G);
``` and wherein X2 is selected from the group consisting of:

```
                                                         (SEQ ID NO: 34)
VEA(L/V)K(K/N)(L/G)(Q/G)(G/N)(R/G)(Q/E)KEVEQ(M/L)R(R/K)A(V/M)RN (Y/F)(A/L)SEALSKI(N/Y)D(L/M)PIT(N/I)DDK(K/E/T/M/Q)L(A/I)SND(V/L)(K/L)K (L/Y)(V/D)A(E/I)(V/A)(W/E)KKLEA(I/M)(L/K)A(-/G/D)(-/S/V)(-/W/E)(-/R/A)
```

-continued (-/W/M)(-/F/A)(-/T)(-/Q)(-/G)(-/S)(-/W)
and (SEQ ID NO: 35)
GS(C/L)SD(I/C)(R/C)KD(C/A)ERRFDKGDGGRKA(M/W)RNFLSE(C/F)LS(C/K)

INDMPITNDDKKL(C/I)SND(L/C)KKY(D/L)AIAEKK(-/G)(-/S)(-W).

In one embodiment, X1 is (SEQ ID NO: 36)
GS(M/L/C)SDIRKD(L/A)E(E/R/)FDKL;

in another embodiment, X1 is (SEQ ID NO: 37)
GS(L/C)SD(I/C)(R/C)KD(A/C)ERRFDKG.

In various further embodiments, the smaller scaffolds comprise or consist of:

RSV_1isea_FFL_005_min_A
(SEQ ID NO: 19)
GSMSDIRKDLEERFDKLVEALKKGQGRQKEVEQMRRAVRNYASEALSKI NDLPITNDDKKLASNDVLKLVAEVWKKLEAILA;
or RSV_1isea_FFL_007_min_A
(SEQ ID NO: 20)
GSLSDIRKDAERRFDKLVEAVKNLGNGEKEVEQLRKAMRNFLSEALSKI

NDMPITNDDKKLISNDLKKYDAIAEKKLEAMKAGSW

RSV_1isea_FFL_005_min_A was designed based on the crystal structure of RSV_1isea_FFL_005, and RSV_1isea_FFL_007_min_A was designed based on the design model for RSV_1isea_FFL_007. In both cases, we eliminated some regions of the parent scaffolds (RSV_1isea_FFL_005 and RSV_1isea_FFL_007) that were not directly contacting the RSV epitope. The total epitope-scaffold length was reduced from 112 to 82 for 005 and 115 to 85 for 007 (excluding the purification tag "LEHHHHHH" (SEQ ID NO: 32) at the Cterminus of each construct). To achieve this we employed a minimization protocol composed of two stages: I) deletion of the coordinates in the PDB file of the residues to be eliminated; II) Backbone rebuilding and sequence design of a new connecting loop between helix 1 and helix 2 in the scaffolds. Residue ranges 25-48 and 104-112 in RSV_1isea_FFL_005 and RSV_1isea_FFL_007 were deleted, and new connecting loops of length 2 or 3 residues were built de novo to create RSV_1isea_FFL_005_min_A and RSV_1isea_FFL_007_min_A.

RSV_1isea_FFL_005_min_A and RSV_1isea_FFL_007_min_A were assessed for their binding to Mota and found to have dissociation constants of 51 and 48 pM, respectively. Thermal stability was also assessed; the melting temperature of RSV_1isea_FFL_007_min_A was 60° C. while the melting temperature for RSV_1isea_FFL_005_min_A was >75° C. but it did not completely melt at the highest temperature tested (98° C.) so the Tm could not be determined with certainty.

In further embodiments, the peptides comprise or consist of:

RSV_1isea_FFL_005_min_A
(SEQ ID NO: 21)
GSMSDIRKDLEERFDKLVEALKKGQGRQKEVEQMRRAVRNYASEALSKI (N/Y)DLPIT(N/I)DDK(K/E/T/M/Q)LASNDVLKLVAEVWKKLEAI LA(D/-)(V/-)(E/-)(A/-)(W/-)(F/-)(T/-)(Q/-)_
or RSV_1isea_FFL_007_min_A
(SEQ ID NO: 22)
GSLSDIRKDAERRFDKLVEAVKNLGNGEKEVEQLRKAMRNFLSEALSKI (N/Y)DMPIT(N/I)DDK(K/E/T/M/Q)LISNDLKKYDAIAEKKLEAM

KA(D/-)(V/-)(E/-)(R/-)(M/-)(A/-)(T/-)(Q/-)GSW

Additional peptides according to the invention are selected from the group consisting of RSV_1ISEA_T_007_23L_D5_C -> combination of 2
disulfides (D1 + D3)
(SEQ ID NO: 23)
GSCSDIRKDCERRFDKGDGGRKAMRNFLSECLSKINDMPITNDDKKLCSN

DLKKYDAIAEKKGSW

RSV_1ISEA_T_007_23L_D6_C -> combination of 2
disulfides (D2 + D3)
(SEQ ID NO: 24)
GSLSDCRKDCERRFDKGDGGRKAMRNFLSECLSCINDMPITNDDKKLISN

DLKKYDAIAEKKGSW

RSV_1ISEA_T2_007_2_D1_C -> extra packed bundle +
D1 disulfide
(SEQ ID NO: 25)
GSCSDIRKDAERRFDKGDGGRKAWRNFLSEFLSKINDMPITNDDKKLCSN

DLKKYLAIAEKK

RSV_1ISEA_T2_007_2_D2_C
(SEQ ID NO: 26)
GSLSDCRKDAERRFDKGDGGRKAWRNFLSEFLSCINDMPITNDDKKLISN

DLKKYLAIAEKK

RSV_1ISEA_T2_007_2_D3_C
(SEQ ID NO: 27)
GSLSDIRKDCERRFDKGDGGRKAWRNFLSECLSKINDMPITNDDKKLISN

DLKKYLAIAEKK

RSV_1ISEA_T2_007_2_D4_C
(SEQ ID NO: 28)
GSLSDICKDAERRFDKGDGGRKAWRNFLSEFLSKINDMPITNDDKKLISN

DCKKYLAIAEKK

These peptides may incorporate one or more of the escape mutants disclosed above, and may incorporate the C-terminal deletion removed from the minimized versions disclosed above.

In a further preferred embodiment, the polypeptide comprises or consists of a sequence selected from the group consisting of SEQ ID NO:4 (FFL_001), SEQ ID NO:5 (FFL_002), SEQ ID NO:7 (FFL_005), SEQ ID NO:8 (FFL_006), SEQ ID NO:9 (FFL_007), SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28. In a more preferred embodiment, the polypeptide comprises or consists of a sequence selected from the group consisting of SEQ ID NO:4 (FFL_001), SEQ ID NO:5 (FFL_002), SEQ ID NO:7 (FFL_005), SEQ ID NO:9 (FFL_007), SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28. In a more preferred embodiment, the polypeptide comprises or consists of a sequence selected from the group consisting of SEQ ID NO:4 (FFL_001), SEQ ID NO:7 (FFL_005), SEQ ID NO:9 (FFL_007) SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28. In a further preferred embodiment the polypeptide comprises or consists of a sequence selected from the group consisting of SEQ ID NO:18, SEQ ID NO:19, SEQ ID NO:20, SEQ ID NO:21, and SEQ ID NO:22. In a further preferred embodiment the polypeptide comprises or consists of a sequence selected from the group consisting of SEQ ID NO:23, SEQ ID NO:24, SEQ ID NO:25, SEQ ID NO:26, SEQ ID NO:27, SEQ ID NO:28.

In a further embodiment, the polypeptide includes any resurfaced version of the listed sequences, referring to resurfacing as described in Correia et al J. Mol Biol 2011 or any related application of the concept of resurfacing.

In a further embodiment, the polypeptide includes any variant of the listed sequences obtained by adding one or more disulfide bonds.

As disclosed herein, the inventors have developed a computational method to design protein scaffolds for epitope conformational stabilization and presentation to the immune system. This method was applied to the Mota epitope to design the polypeptides of the invention, which are shown to be monomeric, highly thermostable, and extremely high binding affinities for Mota.

As used throughout the present application, the term "polypeptide" is used in its broadest sense to refer to a sequence of subunit amino acids. The polypeptides of the invention may comprise L-amino acids, D-amino acids (which are resistant to L-amino acid-specific proteases in vivo), or a combination of D- and L-amino acids. The polypeptides described herein may be chemically synthesized or recombinantly expressed. The polypeptides may contain any suitable linker, etc. for use in any desired application, such as a peptide tag to facilitate polypeptide purification, or a T-help epitope to enhance the desired immune response. For example, two of the exemplified polypeptides discussed below include a C-terminal "GSW" to facilitate determining protein concentration, as those polypeptides did not include any other 'W" residues.

The polypeptides may be linked to other compounds to promote an increased half-life in vivo, such as by PEGylation, HESylation, PASylation, glycosylation, or may be produced as an Fc-fusion or in deimmunized variants. Such linkage can be covalent or non-covalent as is understood by those of skill in the art.

In a further embodiment, the polypeptides of any embodiment of the invention may further comprise a tag, such as a detectable moiety or therapeutic agent. The tag(s) can be linked to the polypeptide through covalent bonding, including, but not limited to, disulfide bonding, hydrogen bonding, electrostatic bonding, recombinant fusion and conformational bonding. Alternatively, the tag(s) can be linked to the polypeptide by means of one or more linking compounds. Techniques for conjugating tags to polypeptides are well known to the skilled artisan. Polypeptides comprising a detectable tag can be used, for example, as probes to isolate B cells that are specific for the epitope present in the polypeptide. However, they may also be used for other detection and/or analytical purposes. Any suitable detection tag can be used, including but not limited to enzymes, prosthetic groups, fluorescent materials, luminescent materials, bioluminescent materials, radioactive materials, positron emitting metals, and nonradioactive paramagnetic metal ions. The tag used will depend on the specific detection/analysis techniques and/or methods used such as flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. When the polypeptides of the invention are used for flow cytometric detections, scanning laser cytometric detections, or fluorescent immunoassays, the tag may comprise, for example, a fluorophore. A wide variety of fluorophores useful for fluorescently labeling the polypeptides of the invention are known to the skilled artisan. When the polypeptides are used for in vivo diagnostic use, the tag can comprise, for example, magnetic resonance imaging (MRI) contrast agents, such as gadolinium diethylenetriaminepentaacetic acid, to ultrasound contrast agents or to X-ray contrast agents, or by radioisotopic labeling.

The polypeptides of the invention can also comprise a tag, such as a linker (including but not limited to an amino acid linker such as cysteine or lysine), for binding to a particle, such as a virus-like particle. As another example, the polypeptides of the invention can usefully be attached to the surface of a microtiter plate for ELISA. The polypeptides of the invention can be fused to marker sequences to facilitate purification, as described in the examples that follow. Examples include, but are not limited to, the hexa-histidine tag, the myc tag or the flag tag.

In another embodiment, a plurality of the polypeptides may be complexed to a dendrimer. Dendrimers are three dimensional, highly ordered oligomeric and/or polymeric compounds typically formed on a core molecule or designated initiator by reiterative reaction sequences adding the oligomers and/or polymers and providing an outer surface. Suitable dendrimers include, but are not limited to, "starburst" dendrimers and various dendrimer polycations. Methods for the preparation and use of dendrimers are well known to those of skill in the art.

In another embodiment, the polypeptides may be fused (via recombinant or chemical means) via their N-terminus, C-terminus, or both N- and C-termini, to an oligomerization domain. Any suitable oligomerization domain can be used. In one non-limiting embodiment, the polypeptides are fused to GCN4 variants that form trimers (hence trimers or hexamers of the fused polypeptide could be displayed). In another non-limiting embodiment, the polypeptides are fused to a fibritin foldon domain that forms trimers. In other non-limiting embodiments, the oligomerization domain could be any protein that assembles into particles, including but not limited to particles made from a (non-viral) lumazine synthase protein and particles made from (non-viral) ferritin or ferritin-like proteins.

In another embodiment, the polypeptides may be chemically conjugated to liposomes. In one non-limiting embodiment, the liposomes contain a fraction of PEGylated lipid in which the PEG groups are functionalized to carry a reactive group, and the polypeptide is chemically linked to the reactive group on the PEG. In another non-limiting embodiment, additional immune-stimulating compounds are included within the liposomes, either within the lipid layers or within the interior. In another non-limiting embodiment, specific cell-targeting molecules are included on the surface of the liposome, including but not limited to molecules that bind to proteins on the surface of dendritic cells.

In another embodiment, a plurality (ie: 2 or more; preferably at least 5, 10, 15, 20, 25, 50, 75, 90, or more copies) of the polypeptides may be present in a virus-like particle (VLP), to further enhance presentation of the polypeptide to the immune system. As used herein, a "virus-like particle" refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified. In a preferred embodiment, the VLP comprises viral proteins that may undergo spontaneous self-assembly, including but not limited to recombinant proteins of adeno associated viruses, rotavirus, recombinant proteins of norwalkvirus, recombinant proteins of alphavirus, recombinant proteins of foot and mouth disease virus, recombinant proteins of retrovirus, recombinant proteins of hepatitis B virus, recombinant proteins of tobacco mosaic virus, recombinant proteins of flock house virus, and recombinant proteins of human papillomavirus, and Qbeta bacteriophage particles. In one preferred embodiment, the viral proteins comprise hepatitis B core antigen particles. In another embodiment, the VLPs are from lipid-enveloped viruses and include lipid as well as any suitable viral protein, including but not limited to proteins from chikungunya virus, or hepatitis B surface antigen proteins. Methods for producing and characterizing recombinantly produced VLPs have been described for VLPs from several viruses, as reviewed in US 20110236408; see also U.S. Pat. No. 7,229,624. As described in the examples that follow, immunization in the context of a VLP with approximately 75 copies of the FFL_001 polypeptide (SEQ ID NO:4) conjugated onto Hepatitis B (HepB) core antigen particles results in an increased immune response to the polypeptide.

The VLPs of the invention can be used as vaccines or antigenic formulations for treating or limiting RSV infection, as discussed herein. In some embodiments, the VLPs may further comprise other scaffolds presenting other epitopes from RSVF or RSVG proteins. In other embodiments, the VLP may further comprise scaffolds presenting epitopes from additional RSV proteins, such as M, N, G, and/or SH.

In another embodiment, the polypeptides may be present on a non-natural core particle, such as a synthetic polymer, a lipid micelle or a metal. Such core particles can be used for organizing a plurality of polypeptides of the invention for delivery to a subject, resulting in an enhanced immune response. By way of example, synthetic polymer or metal core particles are described in U.S. Pat. No. 5,770,380, which discloses the use of a calixarene organic scaffold to which is attached a plurality of peptide loops in the creation of an 'antibody mimic', and U.S. Pat. No. 5,334,394 describes nanocrystalline particles used as a viral decoy that are composed of a wide variety of inorganic materials, including metals or ceramics. Preferred metals in this embodiment include chromium, rubidium, iron, zinc, selenium, nickel, gold, silver, platinum. Preferred ceramic materials in this embodiment include silicon dioxide, titanium dioxide, aluminum oxide, ruthenium oxide and tin oxide. The core particles of this embodiment may be made from organic materials including carbon (diamond). Preferred polymers include polystyrene, nylon and nitrocellulose. For this type of nanocrystalline particle, particles made from tin oxide, titanium dioxide or carbon (diamond) are particularly preferred. A lipid micelle may be prepared by any means known in the art. See U.S. Pat. No. 7,229,624 and references disclosed therein.

In a second aspect, the present invention provides isolated nucleic acids encoding a polypeptide of the present invention. The isolated nucleic acid sequence may comprise RNA or DNA. As used herein, "isolated nucleic acids" are those that have been removed from their normal surrounding nucleic acid sequences in the genome or in cDNA sequences. Such isolated nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. It will be apparent to those of skill in the art, based on the teachings herein, what nucleic acid sequences will encode the polypeptides of the invention.

In a third aspect, the present invention provides recombinant expression vectors comprising the isolated nucleic acid of any aspect of the invention operatively linked to a suitable control sequence. "Recombinant expression vector" includes vectors that operatively link a nucleic acid coding region or gene to any control sequences capable of effecting expression of the gene product. "Control sequences" operably linked to the nucleic acid sequences of the invention are nucleic acid sequences capable of effecting the expression of the nucleic acid molecules. The control sequences need not be contiguous with the nucleic acid sequences, so long as they function to direct the expression thereof. Thus, for example, intervening untranslated yet transcribed sequences can be present between a promoter sequence and the nucleic acid sequences and the promoter sequence can still be considered "operably linked" to the coding sequence. Other such control sequences include, but are not limited to, polyadenylation signals, termination signals, and ribosome binding sites. Such expression vectors can be of any type known in the art, including but not limited plasmid and viral-based expression vectors. The control sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a fourth aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, $2^{nd}$ Ed. (R. I. Freshney. 1987. Liss, Inc. New York, N.Y.). A method of producing a polypeptide according to the invention is an additional part of the invention. The method comprises the steps of (a) culturing a host according to this aspect of the invention under conditions conducive to the expression of the polypeptide, and (b) optionally, recovering the expressed polypeptide. The expressed polypeptide can be recovered from the cell free extract, but preferably they are recovered from the culture medium. Methods to recover polypeptide from cell free extracts or culture medium are well known to the man skilled in the art.

In a fifth aspect, the present invention provides pharmaceutical compositions (such as a vaccine), comprising one or more polypeptides, VLPs, nucleic acids, recombinant expression vectors, or host cells of the invention and a pharmaceutically acceptable carrier. The pharmaceutical compositions of the invention can be used, for example, in the methods of the invention described below. The pharmaceutical composition may comprise in addition to the polypeptide of the invention (a) a lyoprotectant; (b) a surfactant; (c) a bulking agent; (d) a tonicity adjusting agent; (e) a stabilizer; (f) a preservative and/or (g) a buffer.

In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleaste, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The polypeptides may be the sole active agent in the pharmaceutical composition, or the composition may further comprise one or more other agents suitable for an intended use, including but not limited to adjuvants to stimulate the immune system generally and improve immune responses overall. Any suitable adjuvant can be used. The term "adjuvant" refers to a compound or mixture that enhances the immune response to an antigen. Exemplary adjuvants include, but are not limited to, Adju-Phos, Adjumer™, albumin-heparin microparticles, Algal Glucan, Algammulin, Alum, Antigen Formulation, AS-2 adjuvant, autologous dendritic cells, autologous PBMC, Avridine™, B7-2, BAK, BAY R1005, Bupivacaine, Bupivacaine-HCl, BWZL, Calcitriol, Calcium Phosphate Gel, CCR5 peptides, CFA, Cholera holotoxin (CT) and Cholera toxin B subunit (CTB), Cholera toxin A1-subunit-Protein A D-fragment fusion protein, CpG, CRL1005, Cytokine-containing Liposomes, D-Murapalmitine, DDA, DHEA, Diphtheria toxoid, DL-PGL, DMPC, DMPG, DOC/Alum Complex, Fowlpox, Freund's Complete Adjuvant, Gamma Inulin, Gerbu Adjuvant, GM-CSF, GMDP, hGM-CSF, hIL-12 (N222L), hTNF-alpha, IFA, IFN-gamma in pcDNA3, IL-12 DNA, IL-12 plasmid, IL-12/GMCSF plasmid (Sykes), IL-2 in pcDNA3, IL-2/Ig plasmid, IL-2/Ig protein, IL-4, IL-4 in pcDNA3, Imiquimod, ImmTher™, Immunoliposomes Containing Antibodies to Costimulatory Molecules, Interferon-gamma, Interleukin-1 beta, Interleukin-12, Interleukin-2, Interleukin-7, ISCOM(s) ™, Iscoprep 7.0.3™, Keyhole Limpet Hemocyanin, Lipid-based Adjuvant, Liposomes, Loxoribine, LT(R192G), LT-OA or LT Oral Adjuvant, LT-R192G, LTK63, LTK72, MF59, MONTANIDE ISA 51, MONTANIDE ISA 720, MPL™, MPL-SE, MTP-PE, MTP-PE Liposomes, Murametide, Murapalmitine, NAGO, nCT native Cholera Toxin, Non-Ionic Surfactant Vesicles, non-toxic mutant E112K of Cholera Toxin mCT-E112K, p-Hydroxybenzoique acid methyl ester, pCIL-10, pCIL12, pCMVmCAT1, pCMVN, Peptomer-NP, Pleuran, PLG, PLGA, PGA, and PLA, Pluronic L121, PMMA, PODDS™, Poly rA: Poly rU, Polysorbate 80, Protein Cochleates, QS-21, Quadri A saponin, Quil-A, Rehydragel HPA, Rehydragel LV, RIBI, Ribilike adjuvant system (MPL, TMD, CWS), S-28463, SAF-1, Sclavo peptide, Sendai Proteoliposomes, Sendai-containing Lipid Matrices, Span 85, Specol, Squalane 1, Squalene 2, Stearyl Tyrosine, Tetanus toxoid (TT), Theramide™, Threonyl muramyl dipeptide (TMDP), Ty Particles, and Walter Reed Liposomes. Selection of an adjuvant depends on the subject to be vaccinated. Preferably, a pharmaceutically acceptable adjuvant is used.

Compositions comprising the polypeptides can be stored in any standard form, including, e.g., an aqueous solution or a lyophilized cake. Such compositions are typically sterile when administered to cells or subjects. Sterilization of an aqueous solution is readily accomplished by filtration through a sterile filtration membrane. If the composition is stored in lyophilized form, the composition can be filtered before or after lyophilization and reconstitution.

In a sixth aspect, the present invention provides methods for treating and/or limiting an RSV infection, comprising administering to a subject in need thereof a therapeutically effective amount of one or more polypeptides of the invention, salts thereof, conjugates thereof, VLPs thereof, or pharmaceutical compositions thereof, to treat and/or limit the RSV infection. In another embodiment, the method comprises eliciting an immune response in an individual having or at risk of an RSV infection, comprising administering to a subject in need thereof a therapeutically effective amount of one or more polypeptides of the invention, salts thereof, conjugates thereof, VLPs thereof, or pharmaceutical compositions thereof, to generate an immune response.

"Respiratory Syncytial Virus" and "RSV" refer to a negative-sense, single-stranded RNA virus of the family Paramyxoviridae that causes a respiratory disease, especially in children.

When the method comprises treating an RSV infection, the one or more polypeptides, VLPs, or compositions are administered to a subject that has already been infected with the RSV, and/or who is suffering from symptoms (including but not limited to lower respiratory tract infections, upper respiratory tract infections, bronchiolitis, pneumonia, fever, listlessness, diminished appetite, recurrent wheezing, and asthma) indicating that the subject is likely to have been infected with the RSV. As used herein, "treat" or "treating" means accomplishing one or more of the following: (a) reducing RSV titer in the subject; (b) limiting any increase of RSV titer in the subject; (c) reducing the severity of RSV symptoms; (d) limiting or preventing development of RSV symptoms after infection; (e) inhibiting worsening of RSV symptoms; (f) limiting or preventing recurrence of RSV symptoms in subjects that were previously symptomatic for RSV infection. In one embodiment method, polypeptides, VLPs, or compositions are used as "therapeutic vaccines" to ameliorate the existing infection and/or provide prophylaxis against infection with additional RSV virus.

When the method comprises limiting an RSV infection, the one or more polypeptides, VLPs, or compositions are administered prophylactically to a subject that is not known to be infected, but may be at risk of exposure to the RSV. As used herein, "limiting" means to limit RSV infection in subjects at risk of RSV infection. Groups at particularly high risk include children under age 18 (particularly infants 3 years or younger), adults over the age of 65, and individuals suffering from any type of immunodeficiency. In this method, the polypeptides, VLPs, or compositions are used as vaccines.

As used herein, a "therapeutically effective amount" refers to an amount of the polypeptide that is effective for treating and/or limiting RSV infection. The polypeptides are typically formulated as a pharmaceutical composition, such as those disclosed above, and can be administered via any suitable route, including orally, parentally, by inhalation spray, rectally, or topically in dosage unit formulations containing conventional pharmaceutically acceptable carriers, adjuvants, and vehicles. The term parenteral as used herein includes, subcutaneous, intravenous, intra-arterial, intramuscular, intrasternal, intratendinous, intraspinal, intracranial, intrathoracic, infusion techniques or intraperitoneally. Polypeptide compositions may also be administered via microspheres, liposomes, immune-stimulating complexes (ISCOMs), or other microparticulate delivery systems or sustained release formulations introduced into suitable tissues (such as blood). Dosage regimens can be adjusted to provide the optimum desired response (e.g., a therapeutic or prophylactic response). A suitable dosage range may, for instance, be 0.1 ug/kg-100 mg/kg body weight; alternatively, it may be 0.5 ug/kg to 50 mg/kg; 1 ug/kg to 25 mg/kg, or 5 ug/kg to 10 mg/kg body weight. The polypeptides can be delivered in a single bolus, or may be administered more than once (e.g., 2, 3, 4, 5, or more times) as determined by an attending physician.

In certain embodiments, the polypeptides of the invention neutralize RSV infectivity, as demonstrated in the examples that follow. In various embodiments, the polypeptides of the invention prevent RSV from infecting host cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to infection of host cells by RSV in the absence of the polypeptides. Neutralization can be measured using standard techniques in the art.

In another aspect, the present invention provides pharmaceutical composition, comprising (a) isolated nucleic acids, recombinant expression vectors, and/or recombinant host cells of the invention; and (b) a pharmaceutically acceptable carrier. In this aspect, the nucleic acids, expression vectors, and host cells of the invention can be used as polynucleotide-based immunogenic compositions, to express an encoded polypeptide in vivo, in a subject, thereby eliciting an immune response against the encoded polypeptide. Various methods are available for administering polynucleotides into animals. The selection of a suitable method for introducing a particular polynucleotide into an animal is within the level of skill in the art. Polynucleotides of the invention can also be introduced into a subject by other methods known in the art, e.g., transfection, electroporation, microinjection, transduction, cell fusion, DEAE dextran, calcium phosphate precipitation, lipofection (lysosome fusion), or a DNA vector transporter (see, e.g., Wu et al. (1992) J. Biol. Chem. 267:963-967).

The immune response against the polypeptides, VLPs, or compositions of the invention can be generated by one or more inoculations of a subject with an immunogenic composition of the invention. A first inoculation is termed a "primary inoculation" and subsequent immunizations are termed "booster inoculations". Booster inoculations generally enhance the immune response, and immunization regimens including at least one booster inoculation are preferred. Any polypeptide, VLP, or composition of the invention may be used for a primary or booster immunization. The adequacy of the vaccination parameters chosen, e.g., formulation, dose, regimen and the like, can be determined by taking aliquots of serum from the subject and assaying antibody titers during the course of the immunization program. Alternatively, the T cell populations can by monitored by conventional methods. In addition, the clinical condition of the subject can be monitored for the desired effect, e.g., limiting RSV infection, improvement in disease state (e.g., reduction in viral load), etc. If such monitoring indicates that vaccination is sub-optimal, the subject can be boosted with an additional dose of composition, and the vaccination parameters can be modified in a fashion expected to potentiate the immune response. Thus, for example, the dose of the polypeptide, VLP, or composition, and/or adjuvant, can be increased or the route of administration can be changed.

In a further aspect, the present invention provides methods for monitoring an RSV-induced disease in a subject and/or monitoring response of the subject to immunization by an RSV vaccine, comprising contacting the polypeptides, the VLPs, or the pharmaceutical compositions of the invention with a bodily fluid from the subject and detecting RSV-binding antibodies in the bodily fluid of the subject. By "RSV-induced disease" is intended any disease caused, directly or indirectly, by RSV. The method comprises contacting a polypeptide, VLP, or composition of the invention with an amount of bodily fluid (such as serum, whole blood, etc.) from the subject; and detecting RSV-binding antibodies in the bodily fluid of the subject. The detection of the RSV binding antibodies allows the RSV disease in the subject to be monitored. In addition, the detection of RSV binding antibody also allows the response of the subject to immunization by an RSV vaccine to be monitored. In still other methods, the titer of the RSV binding antibodies is determined. Any suitable detection assay can be used, including but not limited to homogeneous and heterogeneous binding immunoassays, such as radioimmunoassays (RIA), ELISA, immunofluorescence, immunohistochemistry, FACS, BIACORE and Western blot analyses. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. The polypeptides of the invention for use in this aspect may comprise a conjugate as disclosed above, to provide a tag useful for any detection technique suitable for a given assay.

In a still further aspect, the present invention provides methods for detecting RSV binding antibodies, comprising
 (a) contacting the polypeptides, the VLPs, or the compositions of the invention with a composition comprising a candidate RSV binding antibody under conditions suitable for binding of RSV antibodies to the polypeptide, VLP, or composition; and
 (b) detecting RSV antibody complexes with the polypeptide, VLP, or composition. In this aspect, the methods are performed to determine if a candidate RSV binding antibody recognizes the RSV F epitope present in the polypeptides of the invention. Any suitable composition may be used, including but not limited to bodily fluid samples (such as serum, whole blood, etc.) from a suitable subject (such as one who has been infected with RSV), naive libraries, modified libraries, and libraries produced directly from human donors exhibiting an RSV-specific immune response. The assays are performed under conditions suitable for promoting binding of antibodies against the polypeptides; such conditions can be determined by those of skill in the art based on the teachings herein. Any suitable detection assay can be used, including but not limited to homogeneous and heterogeneous binding immunoassays, such as radioimmunoassays (RIA), ELISA, immunofluorescence, immunohistochemistry, FACS, BIACORE and Western blot analyses. The methods may be carried in solution, or the polypeptide(s) of the invention may be bound or attached to a carrier or substrate, e.g., microtiter plates (ex: for ELISA), membranes and beads, etc. Carriers or substrates may be made of glass, plastic (e.g., polystyrene), polysaccharides, nylon, nitrocellulose, or teflon, etc. The surface of such supports may be solid or porous and of any convenient shape. The polypeptides of the invention for use in this aspect may comprise a conjugate as disclosed above, to provide a tag useful for any detection technique suitable for a given assay. In a further embodiment, the RSV F-binding antibodies are isolated using standard procedures. In one embodiment, the methods may comprise isolation of polypeptide-specific memory B cells by fluorescence activated cell sorting (FACS) using standard techniques in the art (see, for example, *Science* DOI: 10.1126/science. 1187659)

In another aspect, the present invention provides methods for producing RSV antibodies, comprising
 (a) administering to a subject an amount effective to generate an antibody response of the polypeptides, the VLPs, and/or the compositions of the invention; and
 (b) isolating antibodies produced by the subject.

The polypeptides of the invention can also be used to generate antibodies that recognize the polypeptides of the invention. The method comprises administering to a subject a polypeptide, VLP, or composition of the invention. Such antibodies can be used, for example, in RSV research. A subject employed in this embodiment is one typically employed for antibody production, including but not limited to mammals, such as, rodents, rabbits, goats, sheep, etc. The antibodies generated can be either polyclonal or monoclonal antibodies. Polyclonal antibodies are raised by injecting (e.g. subcutaneous or intramuscular injection) antigenic polypeptides into a suitable animal (e.g., a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

All of the references cited herein are incorporated by reference. Aspects of the disclosure can be modified, if necessary, to employ the systems, functions and concepts of the above references and application to provide yet further embodiments of the disclosure. These and other changes can be made to the disclosure in light of the detailed description.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Example 1

Fold from Loops

The FFL protocol was implemented in the ROSETTA™ software package. The FFL protocol requires as starting inputs a structural motif and a pdb file of the target topology to be folded (FIG. 1). Here, the input structural motif was the RSV peptide-epitope, which has been crystallized in complex with the Fab portion of Motavizumab (PDBid 3IXT). The 3-helix bundle target topology was selected based on the following criteria: the existence of a helix-turn-helix motif in the helical bundle; the high thermal stability of the protein used as the template target topology. The FFL protocol can be partitioned in two-main stages: I) a low-resolution stage with large conformational sampling; II) a full-atom stage with iterations of sequence design and confined conformational sampling.

Low-Resolution Conformational Sampling

Extended polypeptide chains were appended to the termini of the input motif such that the total number of residues matches that of the template topology. The residues of the topology onto which the input motif were inserted were defined through a loop file; the location of the input motif determined the length of the polypeptide chains to append. At this low-resolution stage the representation of the polypeptide chain was coarse-grained; only the atoms of the main chain were explicitly represented and the side chains were represented as spheres.

The conformational sampling carried out at this stage was performed with a Rosetta™ abinitio type protocol. The abinitio protocol relies on the insertion of fragments extracted from a large set of know protein structures. The used fragments were collected with the program NNMAKE™, which builds fragment libraries according to a provided sequence and its secondary structure prediction. For the design work described here the fragments were derived from the sequence of the template.

Optionally, to bias the folding trajectory towards similar structures to that of the target topology, C alpha restraints are extracted [Rohl et al., Methods in Enzymology 383 (2004)] from the target topology and incorporated as a scoring term in the overall scoring function. The Rosetta™ folding protocol which incorporates distance restraints has been previously described by Rohl et al. The distances between residues were collected if sequence separation was larger than 6 and if both residues were outside of the range of the functional site including five residues upstream and downstream. For the designs described here, a standard deviation of 3 Å for each Cα-Cα distance extracted from the template protein was allowed.

In general, throughout the sampling stages the backbone dihedral angles of the input motif were untouched; nevertheless the algorithm implementation allows setting the termini of the motif as moveable. The rationale to allow for these degrees of freedom within the input motif is to favor smooth structural transitions between the input motif and the remaining protein.

Full-Atom Sequence Design and Structural Optimization

After the low-resolution stage during which a large conformational space was explored, the generated models were filtered according to their RMSD relative to the coordinates of native topology. Here, an RMSD threshold of 5 Å was used such that models in the structural vicinity of the target topology would be carried to the sequence design stage, in case a model was above the defined threshold it was automatically discarded. The original side-chain conformations, from the input motif, were recovered and kept fixed throughout the full-atom stage.

By default, in the sequence design stage the 19 amino-acids (cysteine excluded) were allowed in every residue of the models excluding the input functional motif. The exclusion of cysteine is not required. Generally, cysteines are not used for immunogen design unless disulfide bonds are being designed, since immunogens are intended for the extracellular environment which is oxidizing and hence unpaired cysteines in the extracellular environment will tend to form disulfides by paring with other cysteines. For protein design related to intracellular applications, unpaired cysteines are perfectly acceptable. Also at this stage, additional options were implemented for a finer control of the amino-acid identities allowed in particular residue positions. In the FFL designs described here, some positions of the input motif were not part of the antibody-contacting surface and therefore constituted part of the protein core; in some simulations the non contacting side-chains were allowed to change.

After each step of sequence design, a step of full-atom refinement (relax) was performed ensuring that the local conformational space was explored. The relax protocol is composed of several rounds of: small backbone perturbations; side-chain repacking; and energy minimization.

The cycles of iterative sequence design and structural minimization were repeated 3 times. The number of cycles is adjustable by the user.

Design Selection

Quality Filters

Typically 10,000 designs were generated by each FFL run, the first filter applied was based on Rosetta™ full-atom energy, and the best 50 designs by Rosetta Energy™ were further considered. Next, a composite filter was applied to select designs with the best structural features. The structural features considered were: Ramachandran score as implemented in Rosetta™; counts of buried polar atoms not involved in hydrogen bonds; and core packing assessment according to the RosettaHoles™ algorithm. Designed models within the top-25 according to the three features were taken to the next stage.

Some of the designs were selected according the geometrical properties of the models, in particular the bend angle of the helices. Statistics of the bend angles of each helix that composed the helical bundles were collected with the software Helanal™. Bundles with the lowest average bend angle were selected for next stage.

Post-FFL Design

A long identified culprit of the Rosetta™ energy function is the notorious inability to accurately design solvent exposed residues; one of the possible causes is related with the absence of appropriate electrostatics parameterization. To circumvent this known culprit, the first step of post-FFL design was to impose identical residues in the solvent exposed positions as those of the protein used as the template topology.

Next, a step of manual design and all-atom refinement was employed to correct core-packing defects and remove polar amino acids from the core. The manual design was performed to: correct the occurrence of polar residues (in particular histidines) in the designs' cores; and designs straight from the automated stage having alanines overrepresented and valines underrepresented when compared to the template topology. The high frequency of alanines is likely related to the energy term which represents the probability of finding a certain amino-acid given the dihedral angles of the backbone (Ramachandran term), given that the FFL proteins where mostly helical the Ramachandran term will favor the occurrence of alanines and disfavor valines or amino-acids with beta branched side-chains; another potential influencing factor is the proximal arrangement of the helices which in some positions might not allow to fit amino acids larger than alanine.

Given the nature of the iterative design procedure the generated models were highly intolerable to mutations in the core. Consequently, in the manual design stage, steric clashes were introduced by the mutations and a refinement step was necessary for accurate evaluation of the full-atom energies. The refinement served also as a filtering step to the performed manual mutations, as a given mutation or set of mutations would only be accepted if the full atom energy would recover significantly without causing major distortions in the helical local structure. One of the designs (FFL_001) selected for experimental characterization was a straight FFL design with no manual changes performed in the core. This polypeptide was thermodynamically stable and bound the antibody of interest with high affinity.

The designs selected for experimental characterization differed by 6 to 48 mutations when compared to each other. When compared to the sequence of the original template the designs showed between 51 and 59 mutations. A sequence alignment of the FFL designs and the sequence of the original template is shown in FIG. 3.

The backbone rmsds within the designed models were of 0.53 to 3.06 Å and between 1.83 and 2.91 when the designs are compared to the coordinate of the initial template.

Design Minimization

To further reduce the size of the FFL designs, protein segments that didn't contact the mota epitope were eliminated.

Experimental Methods

Expression and Purification

Non-Labeled Protein

DNA segments encoding scaffold constructs were synthesized with optimized codon usage and RNA structure (Codon Devices, Genscript Corp.), subcloned into pET29 (EMD Biosciences) and transformed into Arctic Express™ *E. coli* (Invitrogen). Single colonies were grown overnight at 37° C. in 10 mL Luria Broth (LB) plus Kanamycin (100 mg/ml). The starter cultures were expanded into 1 L of LB plus Kanamycin and incubated at 37° C.; when cells reached log phase, 250 µM of IPTG was added to the cultures to induce protein expression and the cells were then incubated overnight at 12° C. Cultures were then pelleted and resuspended in start buffer (160 mM Imidazole, 4 M Sodium Chloride, 160 mM Sodium Phosphate), a tablet of protease inhibitor (Novagen) was added and the cell suspension was frozen at −20° C.

The cell suspension was thawed and 10 ml of 10× Bugbuster™ (Novagen), 50 µL of Benzonase Nucleases and 1.7 µL of rLysozyme (Novagen) were added to lyse the cells; the cell suspension was then gently tumbled in an orbital shaker for 20 minutes. Lysed cells were pelleted and the supernatant was filtered through a 0.22 µm filter (Millipore). Supernatants were tumbled with 5 mL of Ni++ Sepharose 6 Fast Flow (GE Healthcare) for 1 hour at 4° C. The resin was washed 3 times with 30 mL wash buffer (50 mM imidazole, 500 mM Sodium Chloride and 160 mM Sodium Phosphate) and eluted with 20 mL of Elution Buffer (250 mM Imidazole, 500 mM Sodium Chloride and 20 mM Sodium Phosphate). Fractions containing the construct of interest were combined and further purified by preparative size exclusion chromatography (SEC) on Superdex 75 16/60 (GE Healthcare) at room temperature in HBS. Collected fractions were analyzed on a 4-12% SDS denaturing gel (Invitrogen) and positive fractions were combined and concentrated by ultrafiltration (Vivaspin, Bioexpress). Protein concentration was determined by measuring UV absorption signal at 280 nm (Nanodrop™) and calculated from the theoretical extinction coefficient. To facilitate a rapid and accurate protein quantification the sequence GSW was added to all the designs without tryptophans in their primary sequence.

Low-Endotoxin Protein

In order to prepare low-endotoxin protein for immunization studies, bacterial pellets were alternately resuspended in detergent buffer (50 mM NaH2PO4, 500 mM NaCl, 10 mM imidazole, 0.5 mg/ml lysozyme, 0.01 mg/ml DNase, 0.1% Triton X114) and Ni++ resin was alternately initially washed in 10 mM imidazole, 50 mM NaH2PO4, 500 mM NaCl, 0.1% Triton X114.

N15-Labeled Protein

Isotopically labeled samples of FFL_001, FFL_005, FFL_006 and FFL_007 were grown in minimal MOPS medium supplemented with 1 g/L of $^{15}N$ ammonium chloride. The starter cultures were expanded to 1 L of MOPS and were incubated overnight at 37° C.; 3 ml of 40% $^{15}N$ glucose was added to continue growth, upon reaching an $OD_{\lambda=600}$ 250 µM of IPTG was added to the cultures to induce protein expression and the cells were then incubated overnight at 16° C.

Light Scattering

The monodispersivity and molecular weight of purified proteins were further assessed by HPLC (Agilent, 1200 series) coupled in-line to a static light scattering device (miniDAWN TREOS, Wyatt). 100 µl of 1-2 mg/mL protein sample was used and the collected data was analyzed with the ASTRA™ software (Wyatt).

Circular Dichroism

Solution thermostabilities ($T_m$) were determined by circular dichroism (CD) on an Aviv 62A DS spectrometer. Far-UV wavelength scans (190-260 nm) of 15 to 25 µM protein were collected in a 1 mm path length cuvette. Temperature-induced protein denaturation was followed by change in ellipticity at 210 nm. Experiments were carried over a temperature range from 1-99° C., with 2° C. increments every 3 minutes, and the resulting data was converted to mean residue ellipticity and fitted to a two-state model.

NMR

NMR samples were prepared in 25 mM sodium phosphate, 150 mM NaCl, pH 7.0, and 90% $H_2O$/10% $D_2O$ at a concentration of 500 uM. HSQC spectra for FFL_001, FFL_005, FFL_006 and FFL_007 were recorded on a Bruker Avance™ 600 MHz NMR spectrometer equipped with an actively shielded z-gradient triple resonance cryoprobe. All spectra were recorded at 25° C. Spectra were processed using NMRPipe™ and NMRView™ (1,2).

Surface Plasmon Resonance

All experiments were carried out on a Biacore 2000 (GE Healthcare) at 25° C. with HBSEP (0.01 M HEPES pH 7.4, 0.15 M NaCl, 3 mM EDTA and 0.005% (v/v) Surfactant P20) (GE Healthcare) as running buffer. For binding analysis, 200-500 response units (RUs) of Motavizumab IgG were captured on a CM5 sensor chip containing 8000-9000 RUs of amine-linked mouse anti-human IgG (Human Antibody Capture kit, GE Healthcare). Samples of different protein concentrations were injected in duplicates over this surface at a flow rate of 50-100 µl/min. If necessary, surface regeneration was performed with two 60 seconds injections of 3 M $MgCl_2$ at a flow rate of 10 µl/min. One flow cell contained anti-human IgG only and its interaction with the analyte was used as reference. Alternatively, another format was used where the epitope where amine-coupled to the sensor chip and Mota Fab was injected with identical flow rates as mentioned above.

Data preparation and analysis were performed using Scrubber 2.0 (BioLogic Software). For kinetic analysis, biosensor data were globally fit to a mass transport limited simple bimolecular binding model:

$$A_0 \underset{k_m}{\overset{k_m}{\rightleftharpoons}} A + B \underset{k_{off}}{\overset{k_{on}}{\rightleftharpoons}} AB$$

where $A_0$ represents injected analyte.

Results for Example 1

Figure 2:
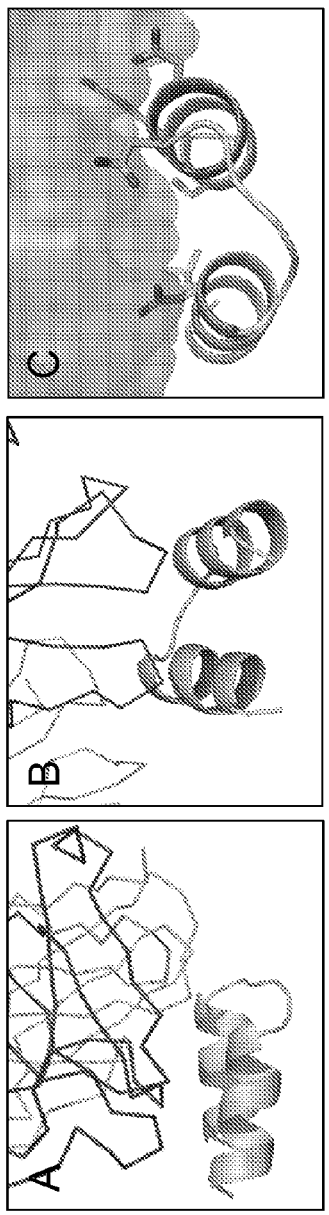
FIG. 2 shows Motavizumab (Mota) in complex with its peptide epitope from the RSVF protein. A) Side-view of the complex. B) Back-view of the complex. C) Side chains on the interface of the complex are shown in sticks.
Figure 5:
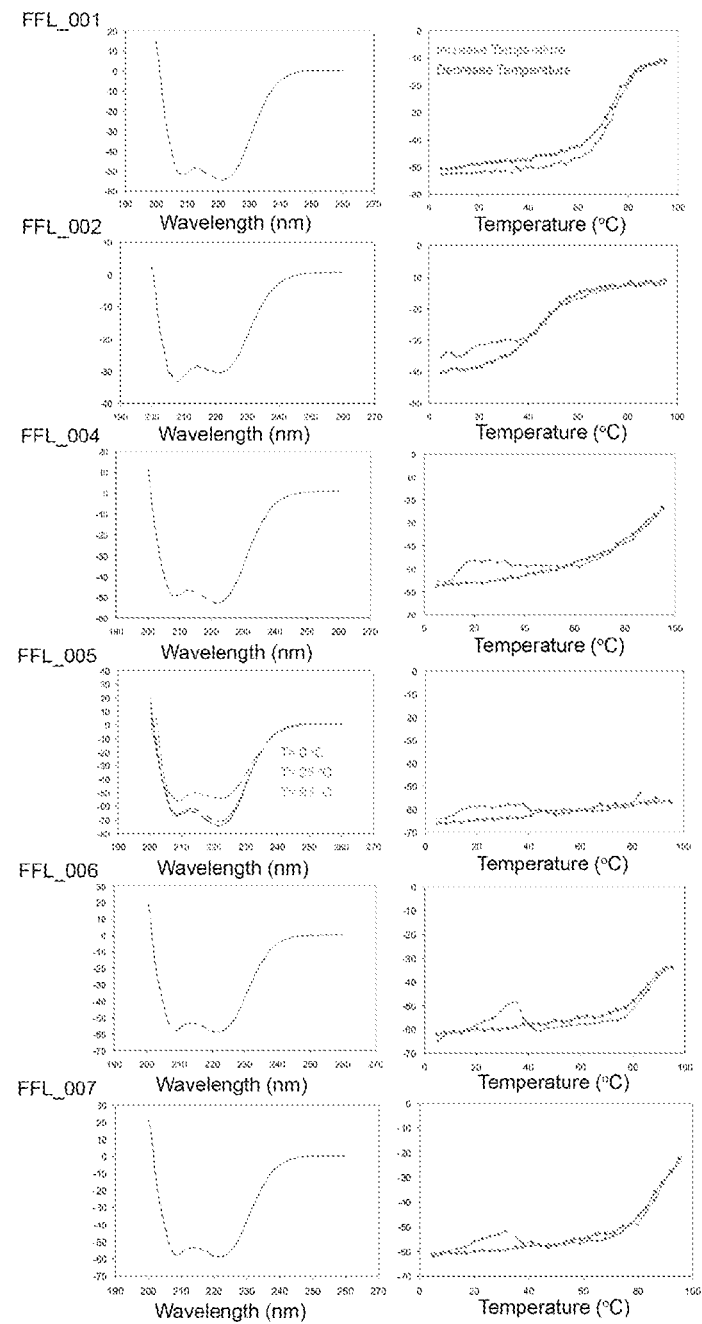
FIG. 5 shows circular dichroism analysis of secondary structure and thermal stability of FFL designs. Wavelength scans (left row) for the designs show the double minima typical for helical proteins. Thermal denaturation curves (right row) indicate cooperative unfolding for most designs, and show that FFL_005 does not melt up to 95° C. The high stability of FFL_005 is exemplified by the wavelength scan at 95° C. (left row). Melting temperatures are given in Table 1.
Figure 6:
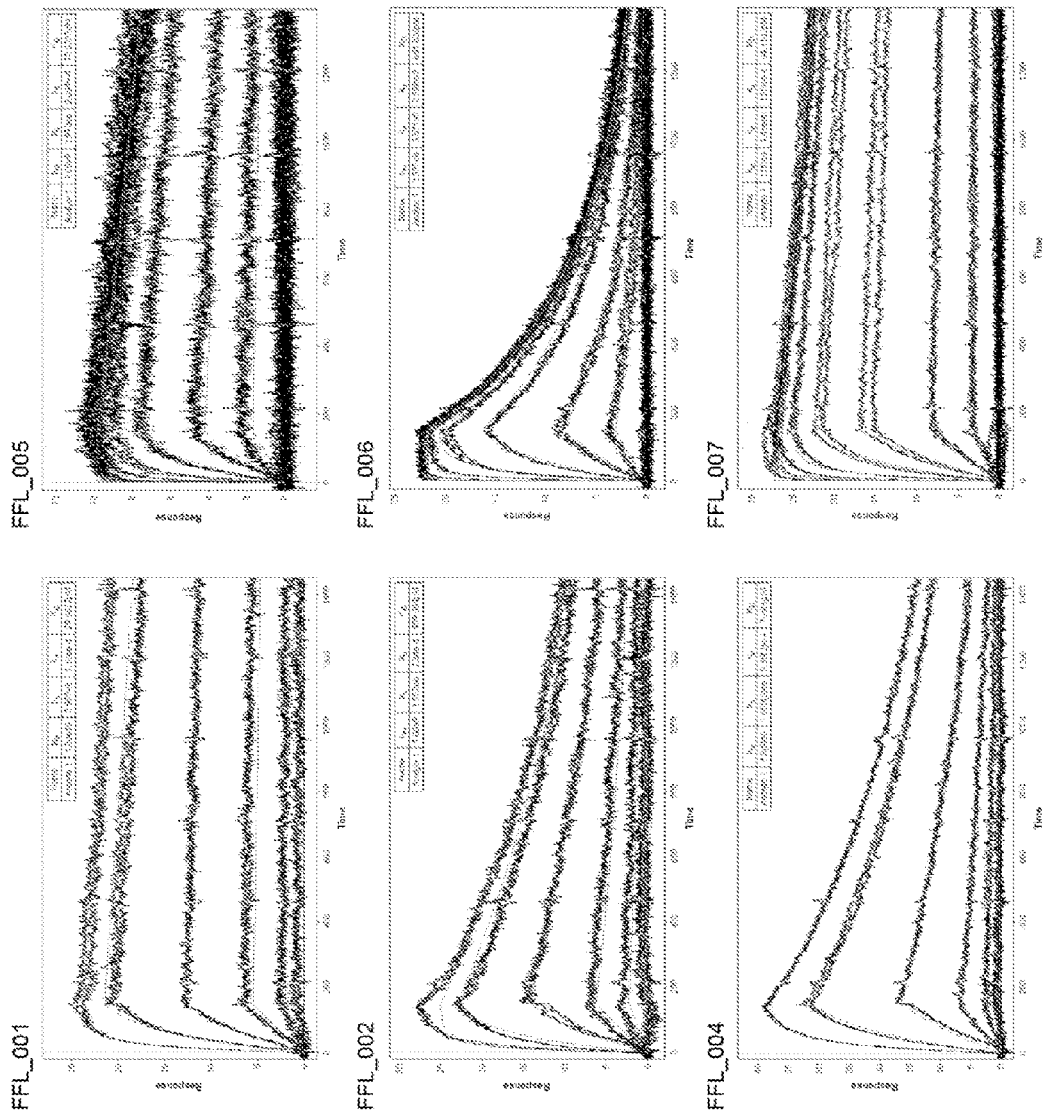
FIG. 6 shows binding of the scaffolds to Motavizumab assessed by SPR. The scaffolds were coupled to the biacore chip and Motavizumab was used as analyte. Both data and kinetic fits are shown. Kinetic fit parameters are given in Table 1.

The structure of the RSV F site A peptide bound to Motavizumab was used as the target binding site for scaffolding. (FIG. 2) This peptide structure (chain P in PDBID: 3IXT) is a helix-turn-helix motif and that led us to choose a three-helix bundle as the target topology for these scaffolds. The structure of PDBID: 3LHP, chain S was selected as the particular three-helix bundle. Procedural details of the FFL designs are shown in Table 1. The different parameters and filtering criteria used on the FFL simulations are summarized. The manual intervention stage is also summarized relative to: number of core mutations performed, the initial Rosetta energy of the designs and the Rosetta energy after the mutations and the full-atom refinement step.

meric protein (≈15 kDa). To evaluate the folding and the thermal stability of the designed molecules we performed circular dichroism spectroscopy (CD) (FIG. 5). The six monomeric designs showed typical CD spectra of properly folded helical proteins. Temperature induced denaturation was followed by CD showing that the stability of the designs ranged from 48 to more than 100° C. (Table 3). To test whether the functional site (mota epitope) was recreated with fidelity, binding affinities were assessed by Surface Plasmon Resonance (SPR) experiments (FIG. 6). The binding constants ($K_D$) were within 30 and 652 pM. (See Table 3) The scaffolds were coupled to the biacore chip and Motavizumab was used as analyte. The binding interaction was readily blocked by a point mutation in the epitope

TABLE 1

| Design | Computational Algorithm SD (Å)[a] | BS design[b] | Filtering Composite Filters | Helix Bend[c] | Manual Intervention Rosetta energy | Mutations | Rosetta energy (post-relax)[d] |
|---|---|---|---|---|---|---|---|
| FFL_001 | 1.5 | X | ✓ | X | — | — | — |
| FFL_002 | 3.0 | ✓ | ✓ | X | −289 | 10 | −276 |
| FFL_003 | 3.0 | ✓ | ✓ | X | −286 | 4 | −293 |
| FFL_004 | 3.0 | ✓ | ✓ | X | −285 | 7 | −291 |
| FFL_005 | 1.5 | ✓ | X | ✓ | −292 | 11 | −287 |
| FFL_006 | 3.0 | ✓ | ✓ | X | −291 | 3 | −290 |
| FFL_007 | 1.5 | ✓ | X | ✓ | −293 | 11 | −285 |
| FFL_008 | 1.5 | ✓ | X | ✓ | −293 | 8 | −286 |

[a]SD—standard deviation allowed to the constraints derived from target topology
[b]BS—Binding site design of the positions that are not in direct contact with the antibody
[c]Filtering criteria based on the helix bend angle as implemented in Helanal
[d]Rosetta energy after the mutations have been performed and a step of full atom optimization Seven scaffolds were designed using the Fold From Loops method (Table 2), and their sequences are shown in FIG. 3 along with the sequence of "T93", the template three-helix bundle from 3LHP.

TABLE 2

Protein scaffolds for the RSV F protein site A epitope

| Protein Scaffold | Reference No. |
|---|---|
| RSVF_siteA_001 | FFL 001 (SEQ ID NO: 4) |
| RSVF_siteA_002 | FFL 002 (SEQ ID NO: 5) |
| RSVF_siteA_003 | FFL 003 (SEQ ID NO: 10) |
| RSVF_siteA_004 | FFL 004 (SEQ ID NO: 6) |
| RSVF_siteA_005 | FFL 005 (SEQ ID NO: 7) |
| RSVF_siteA_006 | FFL 006 (SEQ ID NO: 8) |
| RSVF_siteA_007 | FFL 007 (SEQ ID NO: 9) |
| RSVF_siteA_008 | FFL 008 (SEQ ID NO: 12) |

The designed sequences differ from each other between 8 and 42 mutations. The structural diversity of the computational models varies from each other between 0.53 Å and 3.06 Å.

Figure 4:
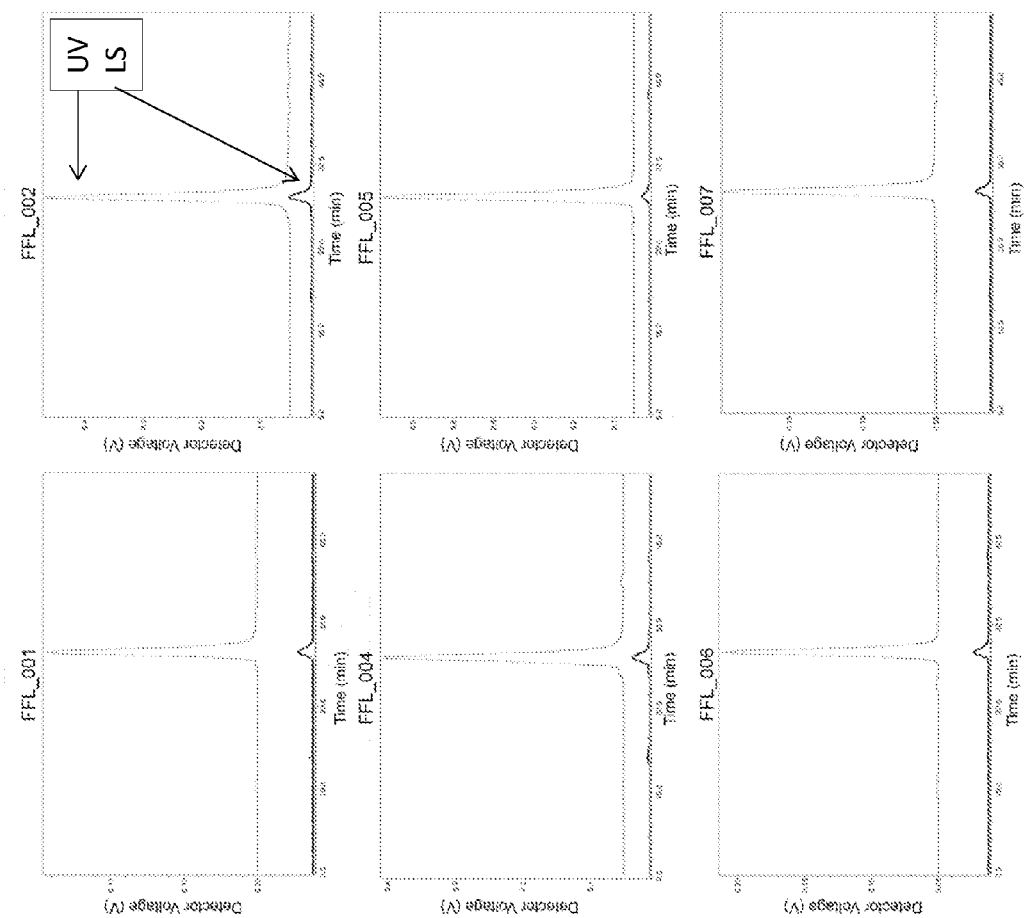
FIG. 4 shows characterization of the oligmeric state of the scaffolds by size exclusion chromatography and static light scattering. All the molecules showed a single monodisperse species and had a molecular weight close to the expected for a monomeric species, approximately 15 kDa. The UV signal from size exclusion is the upper trace in all the graphs, and the light scattering signal is the lower trace.
Figure 7:
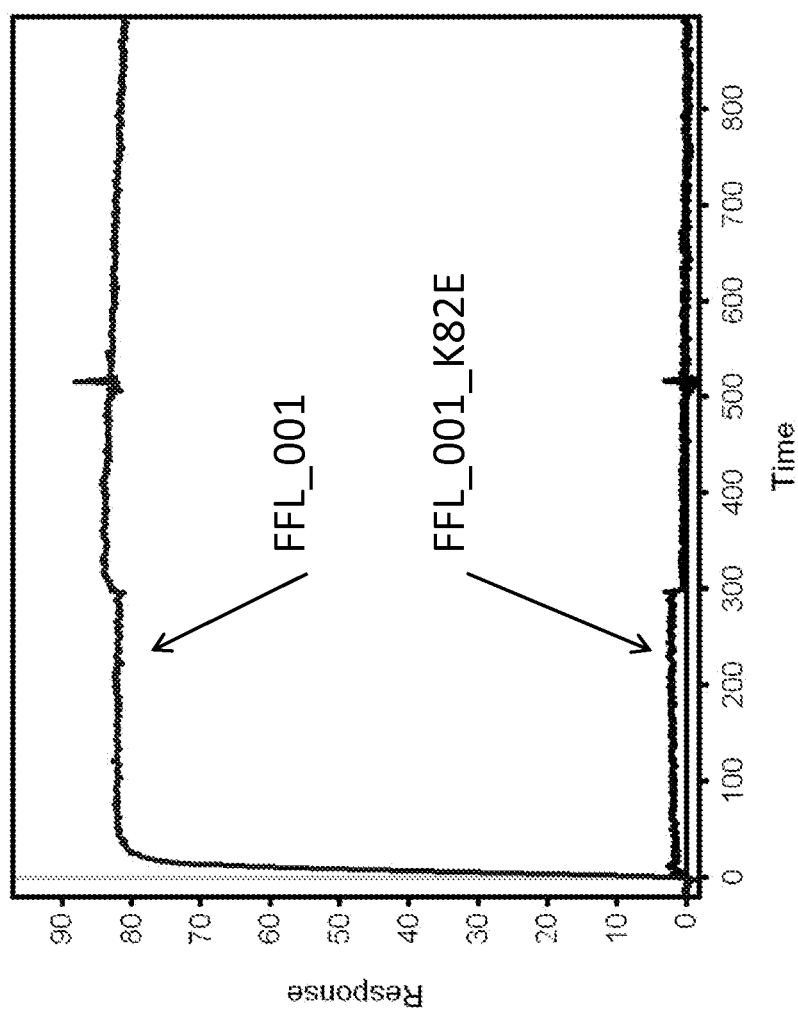
FIG. 7 shows Mota binding specificity of FFL_001 assessed by SPR. Mota IgG was the ligand, captured by anti-human IgG on the sensor chip, and FFL_001 and an epitope point mutant of FFL_001 (FFL_001_K82E) were analytes at a concentration of 22 μM. The interaction between FFL_001 and Mota was eliminated by the point mutation.

To assess expression and solubility, the recombinant proteins were expressed in *E. Coli*, these 7 designed variants were soluble and purifiable through steps of metal affinity chromatography (Ni++) and size exclusion chromatography (SEC) and the yields of expression ranged from 3 to 5 mg L$^{-1}$. To assess the oligomerization state in solution, the seven soluble designs were analyzed by SEC and static light scatter (FIG. 4). Six designs were monodisperse and exhibit an apparent molecular weight corresponding to the monoregion (K28E), previously reported to have the same effect on the RSV context, therefore showing that the binding specificity was directed to the epitope (FIG. 7).

The affinities shown by the best FFL designs represent an improvement by a factor of approximately 7000 over a previously published $K_D$ for the peptide-epitope (200 nM). Recently, a side chain grafting strategy was utilized to transplant the RSV epitope to other heterologous scaffolds (McLellan et al., J. Mol. Biol. (2011) 409, 853-866). In that work, the highest affinity design showed a $K_D$ of 60 nM to the mota antibody. Therefore the FFL designs had KDs improved by a factor of approximately 2000 over the results of McLellan et al.

To obtain an orthogonal characterization of the solution behavior and structural properties of the designed molecules, $^{15}$N-$^1$H hetero-nuclear single-quantum coherence (HSQC) spectra were collected. These spectra showed good peak dispersion typical of protein with well-defined globular folds (not shown). To further evaluate the accuracy of our computational design, an x-ray structure of FFL_005 was solved. The computational model and the crystal structure of FFL_005 (not shown) were in close agreement (1.7 Å rmsd over the backbone atoms), demonstrating the validity of the computational methods for designing polypeptides with a desired structural motif and three-dimensional structure. Furthermore, the conformation of the Mota epitope within the crystal structure of FFL_005 matched the conformation of the Mota-bound peptide from PDB: 3ixt with a rmsd of 0.5 Å, supporting the claim that the FFL method can stabilize the conformation of a structural motif employed as a folding nucleus.

These studies demonstrate successful creation of novel functional proteins by coupling the in silico folding process and sequence design to simultaneously optimize the functional moiety of the molecule and the thermodynamic stability. The described computational strategy is general and flexible such that the target topology is not required to be a naturally occurring protein and back of the envelope topologies can also be used for the design of functionalized proteins. Regarding the structural complexity of the functional sites, the FFL algorithm is suited to deal with discontinuous motifs composed by multiple backbone segments, which are typically required in functional sites of naturally occurring proteins. These results have broad implications for the computational design of functional proteins and the usage of existing protein structures as potential templates.

TABLE 3

Mota binding affinities and thermal stabilities of the FFL designs. The binding affinities were assessed by SPR and the thermal stabilities by CD spectroscopy

| Molecule | $T_m$ (° C.) | SPR $k_{on}$ ($M^{-1}s^{-1}$) | $k_{off}$ ($s^{-1}$) | $k_{off}/k_{on}$ (pM) |
| --- | --- | --- | --- | --- |
| FFL_001 | 75 | $3.99 \times 10^6$ | $1.19 \times 10^{-4}$ | 29.98 |
| FFL_002 | 48 | $1.56 \times 10^6$ | $7.34 \times 10^{-4}$ | 469.9 |
| FFL_004 | >85 | $1.05 \times 10^6$ | $8.32 \times 10^{-4}$ | 795 |
| FFL_005 | >100 | $2.97 \times 10^6$ | $2.09 \times 10^{-4}$ | 70.3 |
| FFL_006 | >85 | $3.57 \times 10^6$ | $2.32 \times 10^{-4}$ | 651.9 |
| FFL_007 | >85 | $1.45 \times 10^6$ | $1.36 \times 10^{-4}$ | 94.1 |

Example 2

FFL_001 scaffolds were conjugated to the surface of HepBcAg particles to improve immune responses to the epitope. The scaffolds were conjugated via hetero-bifunctional cross-linkers between an engineered cysteine in the scaffold at the opposite end from the epitope, and an engineered lysine on the tip of the major immunodominant region of HepBcAg. This oriented the scaffolds in such a way that the epitope was exposed at the radial exterior of the conjugated particle.

Figure 8:
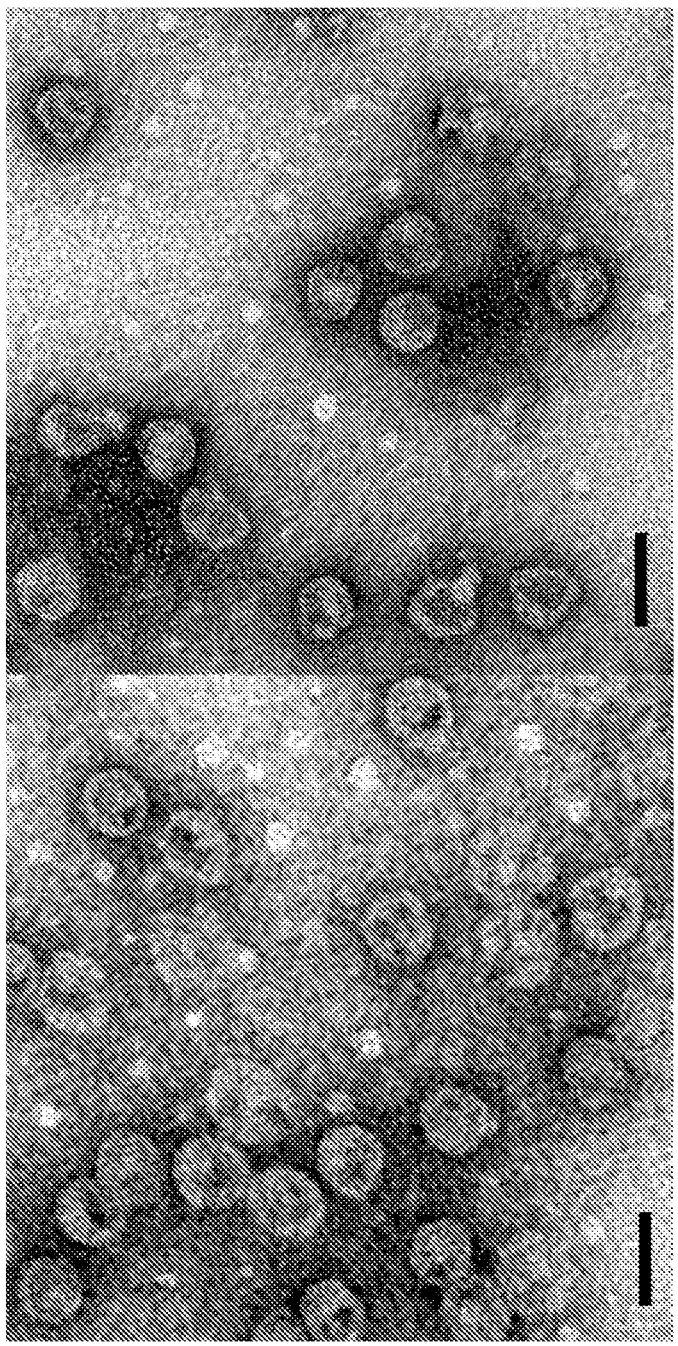
FIG. 8. Negative stain TEM of wild-type (left) and lysine-functionalized (right) HepBcAg particles. Scale bar is 50 nM.

Particles from HBcAg residues 1-149, a construct that leads to higher expression in bacteria and a predominance of the larger T=4 particle with 240 HepBcAg monomers (Zlotnick et al., 1996; Wynne et al., 1999), were expressed in *E. coli* and purified via standard sucrose gradients. For chemical coupling of monomeric FFL immunogens, pure lysine-functionalized HBcAg(1-149) particles were expressed and purified using standard techniques, in which a lysine residue was engineered into the tip of the immunodominant spike of every subunit. HBcAg(1-149) WT and lysine-functionalized particles were both full size (30 nm). (FIG. 8)

Conjugation of FFL_001 scaffolds and HepBcAG were carried out under standard conditions using a 10% Sucrose and 1% CHAPS, resulting in approximately 75 FFL_001 scaffolds attached to each HepB particle, according to densitometry analysis of SDS-PAGE gels run on purified fractions from sucrose gradient ultracentrifugation. Binding Mota to the FFL_001-conjugated particles was evaluated by SPR by capturing Mota IgG on the sensor chip and then binding FFL_001-particles to the Mota IgG-coated surface; subsequently Mota Fab was used as analyte and the kinetics of Mota Fab binding to Mota-IgG-captured-FFL_001-particles were evaluated; in this manner it was confirmed that the FFL_001-conjugated-particles bound to Mota with similar high affinity as FFL_001 monomers (data not shown).

Table 4 summarizes results from a macaque immunization experiment with FFL scaffold monomers and FFL_001-conjugated-HepBcAg-particles. Immunogens were scaffold monomers labeled "001", "005", and "007", and FFL_001-conjugated-HepBcAg-particles labeled "001-particle". Rhesus macaques (4 animals per immunogen) were immunized by the intramuscular route at 0, 1 and 2 months. Animals were injected with 1 mL total volume of antigen mixed with Adjuplex™ adjuvant, with 0.5 mL injected into each arm. The first immunization included a total of 200 ug of scaffold; subsequent immunizations included a total of 100 ug scaffold. "Naïve" sera was taken from each animal on day 0 before the first immunization. "Imm3" sera was taken from each animal 2 weeks after the $3^{rd}$ immunization. Both the "Naïve" and the "Imm3" sera were evaluated for neutralization in a standard plaque reduction assay at a serum dilution of 1:20. Each sample was run in duplicate (counts for the two individual runs are shown as "Naive1", "Naive2", "Imm3_1", and "Imm3_2". The average plaque counts "Naïve_ave" and "Imm3_ave" were computed from the two runs. The % plaque reduction was calculated as (Naïve_ave−Imm3_ave)/Naïve_ave. The sera were also tested for ELISA reactivity to recombinant RSVF protein. The endpoint titers are given for each animal. The % plaque reduction numbers show a modest linear correlation with the ELISA titers, with a Pearson coefficient of 0.58.

These data demonstrate that macaque immunization with FFL scaffold monomers or FFL scaffolds presented on HepBcAg particles can result in the production of RSVF-binding antibodies and RSV neutralizing antibodies. The % neutralization (% plaque reduction) was as high as 88% for particle-displayed scaffolds, and as high as 72% for monomeric scaffolds. The average % plaque reduction for VLP-presented scaffolds was 51±25%, which was higher than the average for any of the monomer samples, the highest % plaque reduction for a monomer sample being 33±11% for FFL_001 monomers. The difference in the average % plaque reduction for particle-001 compared to monomer-001 was not statistically significant. The average RSVF ELISA titer was also higher for the particle-001 sample (94000±20000) compared to the highest titer monomer sample (79000±66000 for FFL_001), but again the difference was not statistically significant.

TABLE 4

| Immunogen | NHP id | % plaque reduction | RSVF ELISA titer | Naïve_ave | Naive 1 | Naive 2 | Imm3_ave | Imm3_1 | Imm3_2 |
| --- | --- | --- | --- | --- | --- | --- | --- | --- | --- |
| 001-particle | D039 | 0.8757 | 120000 | 84.5 | 83 | 86 | 10.5 | 13 | 8 |
| 007 | D030 | 0.717 | 110000 | 79.5 | 80 | 79 | 22.5 | 21 | 24 |
| 005 | D180 | 0.5924 | 22000 | 78.5 | 72 | 85 | 32 | 35 | 29 |
| 001 | C012 | 0.4536 | 170000 | 91.5 | 89 | 94 | 50 | 46 | 54 |

TABLE 4-continued

| Immunogen | NHP id | % plaque reduction | RSVF ELISA titer | Naïve_ave | Naive 1 | Naive 2 | Imm3_ave | Imm3_1 | Imm3_2 |
|---|---|---|---|---|---|---|---|---|---|
| 001-particle | C004 | 0.4491 | 93000 | 83.5 | 74 | 93 | 46 | 50 | 42 |
| 001-particle | D130 | 0.4207 | 91000 | 72.5 | 68 | 77 | 42 | 43 | 41 |
| 007 | D227 | 0.3716 | 23000 | 91.5 | 84 | 99 | 57.5 | 57 | 58 |
| 007 | C010 | 0.3709 | 36000 | 75.5 | 70 | 81 | 47.5 | 44 | 51 |
| 001 | D027 | 0.3642 | 12000 | 75.5 | 81 | 70 | 48 | 46 | 50 |
| 001 | D052 | 0.3243 | 65000 | 92.5 | 89 | 96 | 62.5 | 63 | 62 |
| 001-particle | D184 | 0.3038 | 72000 | 79 | 72 | 86 | 55 | 52 | 58 |
| 005 | D104 | 0.2 | 8500 | 67.5 | 64 | 71 | 54 | 54 | 54 |
| 001 | D172 | 0.1954 | 69000 | 87 | 88 | 86 | 70 | 65 | 75 |
| 005 | D190 | 0.1931 | 4800 | 72.5 | 68 | 77 | 58.5 | 50 | 67 |
| 005 | D032 | 0.1243 | 9500 | 88.5 | 85 | 92 | 77.5 | 78 | 77 |
| 007 | D087 | 0.047 | 15000 | 74.5 | 73 | 76 | 71 | 70 | 72 |

We claim:

1. An isolated polypeptide comprising the amino acid sequence selected from the group consisting of SEQ ID NOS:4-28.

2. The isolated polypeptide of claim 1, wherein the polypeptide comprises a sequence selected from the group consisting of SEQ ID NO:4, SEQ ID NO:5, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28.

3. The isolated polypeptide of claim 1, wherein the polypeptide comprises a sequence selected from the group consisting of SEQ ID NO:4, SEQ ID NO:7, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, and SEQ ID NO:28.

4. An isolated nucleic acid encoding the polypeptide of claim 1.

5. A recombinant expression vector comprising the isolated nucleic acid of claim 4 operatively linked to a promoter.

6. A recombinant host cell comprising the recombinant expression vector of claim 5.

7. A pharmaceutical composition, comprising the polypeptide of claim 1, and a pharmaceutically acceptable carrier.

* * * * *